(12) United States Patent
Smith et al.

(10) Patent No.: US 8,702,804 B2
(45) Date of Patent: Apr. 22, 2014

(54) VARIABLE PROSTHESIS

(75) Inventors: Aaron P. Smith, Warsaw, IN (US);
Kevin T. Stone, Winona Lake, IN (US);
Nicholas Cordaro, Vista, CA (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/309,973

(22) Filed: Dec. 2, 2011

(65) Prior Publication Data

US 2013/0144397 A1   Jun. 6, 2013

(51) Int. Cl.
*A61F 2/38* (2006.01)
*A61F 2/40* (2006.01)
*A61F 2/32* (2006.01)
*A61F 2/42* (2006.01)
*A61F 2/36* (2006.01)

(52) U.S. Cl.
USPC ........... 623/20.35; 623/23.65; 623/22.42; 623/22.43; 623/22.45; 623/22.46; 623/19.11; 623/19.12; 623/19.13; 623/19.14; 623/22.11; 623/22.15; 623/22.4; 623/23.11; 623/22.14

(58) Field of Classification Search
USPC .......................................... 623/20.35, 23.65
See application file for complete search history.

(56) References Cited

U.S. PATENT DOCUMENTS

| | | |
|---|---|---|
| 3,815,157 A | 6/1974 | Skorecki et al. |
| 3,842,442 A | 10/1974 | Kolbel et al. |
| 3,916,451 A | 11/1975 | Buechel et al. |
| 3,978,528 A | 9/1976 | Crep |
| 3,979,778 A | 9/1976 | Stroot |
| 4,003,095 A | 1/1977 | Gristina |
| 4,030,143 A | 6/1977 | Elloy et al. |
| 4,040,131 A | 8/1977 | Gristina |
| 4,135,517 A | 1/1979 | Reale |
| 4,179,758 A | 12/1979 | Gristina |
| 4,206,517 A | 6/1980 | Pappas et al. |
| 4,693,723 A | 9/1987 | Gabard et al. |
| 4,822,370 A | 4/1989 | Schelhas |
| 4,865,605 A | 9/1989 | Dines et al. |
| 4,865,609 A | 9/1989 | Roche |
| 4,919,670 A | 4/1990 | Dale et al. |

(Continued)

FOREIGN PATENT DOCUMENTS

| | | |
|---|---|---|
| DE | 19509037 | 9/1996 |
| EP | 0257359 A1 | 3/1988 |

(Continued)

OTHER PUBLICATIONS

"Buechel-Pappas.TM. Total Shoulder System", Endotec, Jul. 1991.

(Continued)

*Primary Examiner* — Thomas J Sweet
*Assistant Examiner* — Krutanjali M Shah
(74) *Attorney, Agent, or Firm* — Harness, Dickey

(57) ABSTRACT

The present teachings are directed to a shoulder prosthesis having an adjustable radial offset and/or angular inclination provided by relative rotation of an adapter interdisposed between a stem and a head. In one example, a prosthesis has a stem having a first longitudinal axis. The prosthesis can also include an adaptor including a first taper. The first taper can have a first taper axis. The prosthesis can include a head supported by the adaptor. The head can be selectively oriented and then coupled to the first taper and the combination can be selectively orientated and the coupled to the stem.

20 Claims, 13 Drawing Sheets

(56) References Cited

U.S. PATENT DOCUMENTS

| | | | |
|---|---|---|---|
| 4,957,510 | A | 9/1990 | Cremascoli |
| 4,963,155 | A | 10/1990 | Lazzeri et al. |
| 5,080,673 | A | 1/1992 | Burkhead et al. |
| 5,080,685 | A | 1/1992 | Bolesky et al. |
| 5,135,529 | A | 8/1992 | Paxson et al. |
| 5,181,928 | A | 1/1993 | Bolesky et al. |
| 5,201,882 | A | 4/1993 | Paxson |
| 5,222,984 | A | 6/1993 | Forte |
| 5,314,479 | A | 5/1994 | Rockwood, Jr. et al. |
| 5,358,526 | A | 10/1994 | Tornier |
| 5,462,563 | A | 10/1995 | Shearer et al. |
| 5,507,817 | A | 4/1996 | Craig et al. |
| 5,507,818 | A | 4/1996 | McLaughlin |
| 5,507,824 | A | 4/1996 | Lennox |
| 5,549,682 | A | 8/1996 | Roy |
| 5,580,352 | A | 12/1996 | Sekel |
| 5,702,457 | A | 12/1997 | Walch et al. |
| 5,702,486 | A | 12/1997 | Craig et al. |
| 5,723,018 | A | 3/1998 | Cyprien et al. |
| 5,728,161 | A | 3/1998 | Camino et al. |
| 5,776,194 | A | 7/1998 | Mikol et al. |
| 5,902,340 | A | 5/1999 | White et al. |
| 5,910,171 | A | 6/1999 | Kummer et al. |
| 5,961,555 | A | 10/1999 | Huebner |
| 6,033,439 | A | 3/2000 | Camino et al. |
| 6,045,582 | A | 4/2000 | Prybyla |
| 6,102,953 | A | 8/2000 | Huebner |
| 6,129,764 | A | 10/2000 | Servidio |
| 6,171,341 | B1 | 1/2001 | Boileau et al. |
| 6,197,062 | B1 | 3/2001 | Fenlin |
| 6,197,063 | B1 | 3/2001 | Dews |
| 6,206,925 | B1 | 3/2001 | Tornier |
| 6,228,120 | B1 | 5/2001 | Leonard et al. |
| 6,364,910 | B1 | 4/2002 | Shultz et al. |
| 6,368,352 | B1 | 4/2002 | Camino et al. |
| 6,530,957 | B1 | 3/2003 | Jack |
| 6,620,197 | B2 | 9/2003 | Maroney et al. |
| 6,626,946 | B1 | 9/2003 | Walch et al. |
| 6,719,799 | B1 | 4/2004 | Kropf et al. |
| 6,736,852 | B2 | 5/2004 | Callaway et al. |
| 6,761,740 | B2 | 7/2004 | Tornier et al. |
| 6,790,234 | B1 | 9/2004 | Frankle |
| 6,890,358 | B2 | 5/2005 | Ball et al. |
| 6,942,699 | B2 | 9/2005 | Stone et al. |
| 6,974,483 | B2 * | 12/2005 | Murray ............... 623/22.42 |
| 6,986,790 | B2 | 1/2006 | Ball et al. |
| 7,022,141 | B2 | 4/2006 | Dwyer et al. |
| 7,097,663 | B1 | 8/2006 | Nicol et al. |
| 7,135,044 | B2 | 11/2006 | Bassik et al. |
| 7,175,663 | B1 | 2/2007 | Stone |
| 7,189,261 | B2 | 3/2007 | Dews et al. |
| 7,238,207 | B2 | 7/2007 | Blatter et al. |
| 7,819,823 | B2 * | 10/2010 | Lehrman et al. ............ 600/586 |
| 7,819,923 | B2 * | 10/2010 | Stone et al. ............... 623/19.14 |
| 8,088,169 | B2 * | 1/2012 | Dorr et al. ............... 623/23.59 |
| 2001/0049561 | A1 | 12/2001 | Dews et al. |
| 2001/0053935 | A1 | 12/2001 | Hartdegen et al. |
| 2002/0120339 | A1 | 8/2002 | Callaway et al. |
| 2002/0138148 | A1 | 9/2002 | Hyde |
| 2002/0156534 | A1 | 10/2002 | Grusin et al. |
| 2003/0028253 | A1 | 2/2003 | Stone et al. |
| 2003/0074079 | A1 * | 4/2003 | McTighe et al. .......... 623/22.42 |
| 2003/0097183 | A1 | 5/2003 | Rauscher et al. |
| 2003/0114933 | A1 | 6/2003 | Bouttens et al. |
| 2003/0158605 | A1 | 8/2003 | Tornier |
| 2004/0064189 | A1 | 4/2004 | Maroney et al. |
| 2004/0064190 | A1 | 4/2004 | Ball et al. |
| 2004/0138757 | A1 * | 7/2004 | Nadzadi et al. ............ 623/22.11 |
| 2004/0220673 | A1 | 11/2004 | Pria |
| 2004/0220674 | A1 | 11/2004 | Pria |
| 2005/0197708 | A1 | 9/2005 | Stone et al. |
| 2006/0020344 | A1 | 1/2006 | Shultz et al. |
| 2006/0106463 | A1 * | 5/2006 | Bigsby et al. ............ 623/23.42 |
| 2007/0005145 | A1 * | 1/2007 | Banks et al. ............. 623/23.42 |
| 2007/0043446 | A1 * | 2/2007 | Murray ................... 623/22.12 |
| 2007/0043448 | A1 * | 2/2007 | Murray ................... 623/22.46 |
| 2007/0142918 | A1 | 6/2007 | Stone |
| 2007/0198094 | A1 | 8/2007 | Berelsman et al. |
| 2007/0219641 | A1 * | 9/2007 | Dorr et al. ............... 623/22.42 |
| 2008/0234830 | A1 * | 9/2008 | Hershberger et al. ...... 623/22.15 |
| 2009/0192621 | A1 | 7/2009 | Winslow et al. |
| 2009/0210065 | A1 | 8/2009 | Nerot et al. |
| 2009/0270993 | A1 | 10/2009 | Maisonneuve et al. |
| 2010/0152860 | A1 | 6/2010 | Brooks et al. |
| 2010/0168865 | A1 | 7/2010 | Birkbeck et al. |
| 2010/0179664 | A1 | 7/2010 | Brooks et al. |
| 2011/0035013 | A1 | 2/2011 | Winslow et al. |
| 2011/0035015 | A1 | 2/2011 | Stone et al. |
| 2011/0054624 | A1 | 3/2011 | Iannotti |
| 2011/0118846 | A1 | 5/2011 | Katrana et al. |
| 2012/0065737 | A1 * | 3/2012 | Chow ................... 623/22.42 |
| 2012/0078375 | A1 * | 3/2012 | Smith et al. ............... 623/20.35 |

FOREIGN PATENT DOCUMENTS

| | | |
|---|---|---|
| EP | 0599429 A2 | 6/1994 |
| EP | 0664108 A2 | 7/1995 |
| EP | 0679375 A1 | 11/1995 |
| EP | 0712617 A1 | 5/1996 |
| EP | 0797964 A1 | 10/1997 |
| EP | 1472999 A1 | 11/2004 |
| EP | 1520560 A1 | 4/2005 |
| EP | 1639965 | 3/2006 |
| FR | 2574283 A1 | 6/1986 |
| FR | 2652498 A1 | 4/1991 |
| FR | 2664809 A1 | 1/1992 |
| FR | 2704747 | 11/1994 |
| FR | 2721200 A1 | 12/1995 |
| FR | 2848099 | 6/2004 |
| FR | 2852229 A1 | 9/2004 |
| GB | 2405346 | 3/2005 |
| WO | WO-9522302 A1 | 8/1995 |
| WO | WO-9617553 A1 | 6/1996 |
| WO | WO-9846172 A1 | 10/1998 |
| WO | WO-0015154 A1 | 3/2000 |

OTHER PUBLICATIONS

"Delta Prothese Totale D'epaule Inversee", Depuy 2005 (8 sheets).

"Magnum™, M2a-Magnum™ Operative Technique," brochure. Biomet UK Ltd. (2008) pp. 1-14.

"Reverse Shoulder Prosthesis", Encore Surgical, 2004 (2 sheets).

European Search Report for EP06254735 mailed Apr. 5, 2007.

Final Office Action for U.S. Appl. No. 11/234,743 Mailed Jun. 15, 2010.

Final Office Action for U.S. Appl. No. 12/911,238 Mailed Dec. 1, 2011.

International Search Report for PCT/US02/22040 mailed Apr. 4, 2003.

M2a-Magnum™, "Large Metal Articulation," brochure. Biomet (2001), 8 sheets.

Non-Final Office Action for U.S. Appl. No. 11/234,743 Mailed Dec. 2, 2009.

Non-Final Office Action for U.S. Appl. No. 11/234,743 Mailed Dec. 21, 2010.

Non-Final Office Action for U.S. Appl. No. 12/911,238 Mailed Jul. 1, 2011.

Non-Final Office Action for U.S. Appl. No. 12/390,652 Mailed Feb. 28, 2011.

Surgery Eases Rotator Cuff Pain by Ruth Campbell Odessa American, online article, (2 sheets) dated Feb. 9, 2009.

Thabe et al., "Die endoprothetische Versorgung des rheumatischen Schultergelenkes", Aktuelle Rheumatologie, vol. 19 (1994), pp. 155-160 (with English abstract).

Thabe et al., "Modulares—Vario—Schulter", 1999, 6 sheets of pictures.

The Delta CTA™ Reverse Shoulder System, copyright Johnson & Johnson Gateway LLC 2000-2005 online article (2 sheets) dated Feb. 9, 2005.

* cited by examiner

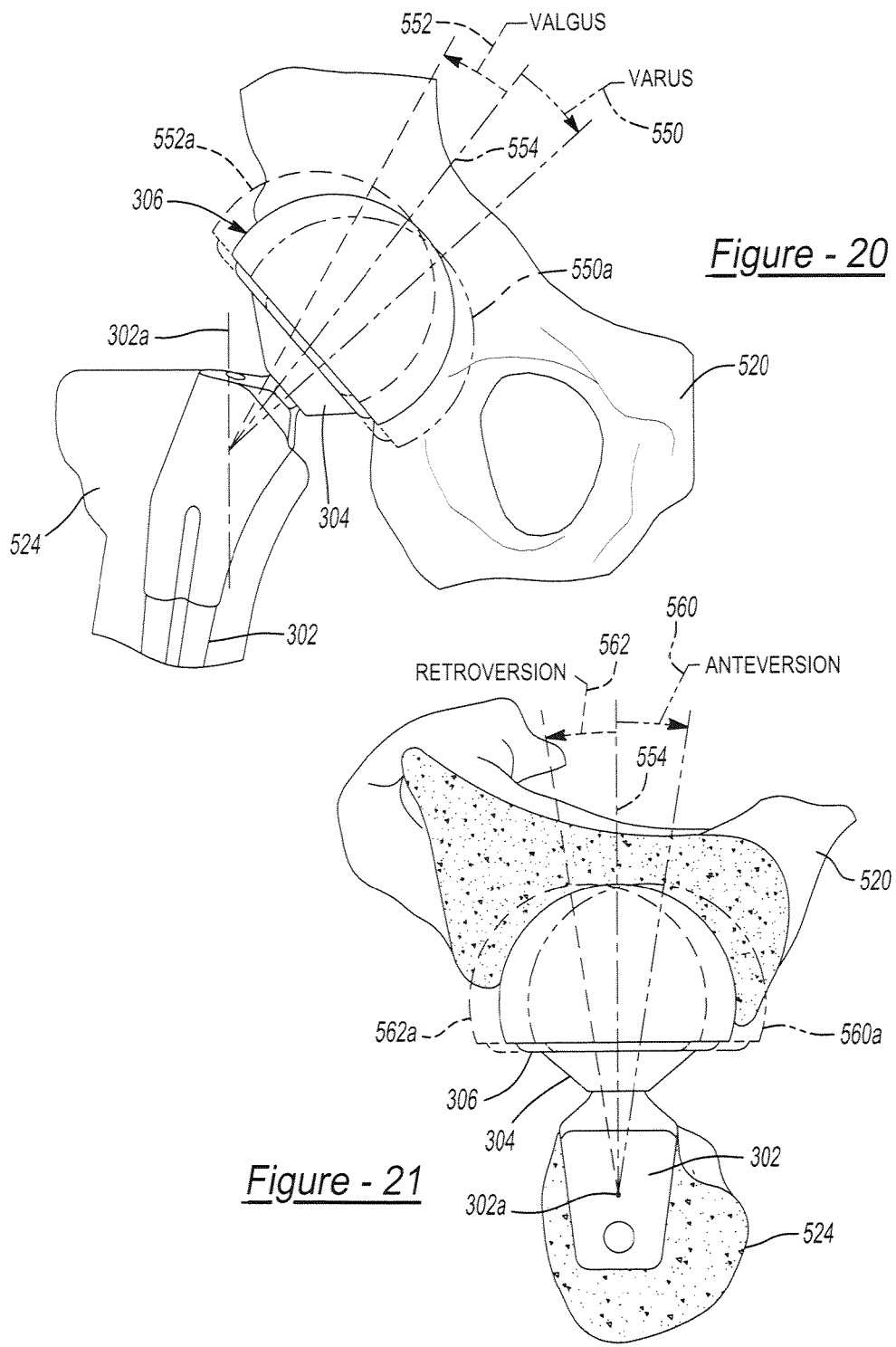

VARIABLE PROSTHESIS

BACKGROUND

The present teachings relate to a prosthesis for replacing and reconstructing a portion of the joint and more specifically to a modular prosthesis.

The shoulder joint is considered to be one of the most complex joints in the body. The scapula, the clavicle and the humerus all meet at the shoulder joint. The head of the humerus fits into a shallow socket of the scapula called the glenoid fossa to form a mobile joint. When the joint is articulated, the humeral head moves in the glenoid fossa to provide a wide range of motion. The shoulder joint may suffer from various maladies including rheumatoid arthritis, osteoarthritis, rotator cuff arthroplasty, a vascular necrosis, bone fracture or failure of previous joint implants. If severe joint damage occurs and no other means of treatment is found to be effective, then a total shoulder reconstruction may be necessary.

A shoulder joint prosthesis generally includes the replacement of the ball of the humerus and, optionally, the socket of the shoulder blade with specially designed artificial components. The bio-kinematics, and thus the range of motion in the shoulder vary greatly among prospective patients for reconstruction shoulder surgery. The humeral component typically has a metal shaft or stem with a body portion that is embedded in the resected humerus and a generally hemispherical head portion supported on the stem. The head slidingly engages a glenoid implant on the glenoid fossa. During reconstructive surgery, the components of the prosthesis are matched with the bio-kinematics of the patient in an effort to maintain the natural range of motion of a healthy shoulder joint. Thus, a shoulder prosthesis design must be readily adaptable to a wide range of bio-kinematics for prospective patients.

In this regard, shoulder prostheses are generally available as either unitary structures or modular components. With unitary shoulder prosthesis, a large inventory of differently sized prostheses must be maintained to accommodate the different bone sizes and joint configurations of the prospective patients. With such unitary shoulder prosthesis, the patient is typically evaluated by x-ray to determine the approximate prostheses size needed for reconstruction. A number of differently sized prostheses are selected as possible candidates based upon this preliminary evaluation. Final selection of the appropriately sized prosthesis is made during the surgery. With unitary shoulder prosthesis, each design represents a compromise that is unable to achieve all of the natural range of motion of a healthy shoulder joint because of the fixed geometric configuration in their design.

Modular prostheses systems which reduce the need to maintain large inventories of various sized components are well known in the art. Conventionally, the humeral prosthesis includes two components—a humeral stem component and a spherical head releasably coupled to the stem. Alternately, a three component design is known in which the stem and shoulder are interconnected with an adapter. In either of the two-piece or three-piece designs, a radial offset or angulator inclination of the head relative to the stem is provided in individual components. For example, in the three-piece design, an adapter may be configured with a fixed radial offset of 2 millimeters or an angular inclination of 5 degrees. Different radial offsets or angular inclinations are achieved through the use of different adapters or heads. In this regard, conventional modular shoulder prosthesis kits include multiple redundant components such as adapters and heads to achieve a range of prosthetic options. While providing an advantage over the unitary design in reducing the number of components needed, a rather large inventory of head components and/or adapter components must be maintained to provide the desired range of geometric configurations with the conventional modular shoulder prostheses. Therefore, there is a need for modular shoulder prostheses which are readily adaptable to provide a range of geometric configurations, i.e. radial offsets of angular inclination while minimizing the number of components required.

SUMMARY

In accordance with the present teachings, a modular joint prosthesis system is provided. Specifically, a humeral component for a total shoulder prosthesis includes an adapter and a head component which cooperate to provide a range of radial offsets and/or angular inclinations and which are adapted to be used in conjunction with a stem.

In one embodiment, a humeral component for a total shoulder prosthesis is provided for adjustable radial offset of the head with respect to the stem. The shoulder prosthesis includes an adapter interposed between a stem and a head. The adapter is eccentrically coupled to the stem such that relative angular positioning of the adapter on the stem will effect a first adjustment in the radial offset. Likewise, the head component is eccentrically coupled to the adapter as such that relative angular position of the head on the adapter will effect a second radial offset adjustment. By selectively positioning the adapter and the head component with respect to the stem, an infinite adjustment of the radial offset within a given range may be achieved. In one example, indicia are provided at the interface between the adapter and the head to indicate the offset vector (i.e., offset amount and direction).

In another embodiment, a humeral component for a total shoulder prosthesis is provided for adjustable angular inclination of the head component relative to the stem component. The shoulder prosthesis includes an adapter interposed between a stem and a head. The adapter is coupled to the stem in a first angled or non-orthogonal orientation such that relative rotational positioning of the adapter on the stem will effect a first adjustment in the direction of the angular inclination. Likewise, the adapter is coupled to the head in a second angled or non-orthogonal orientation as such that relative rotational position of the head on the adapter will effect a second adjustment in the direction of the angular inclination. By selectively positioning the adapter and the head component with respect to the stem, an infinite adjustment of the angular inclination within a given range may be achieved.

In yet another embodiment, the present teachings include an adapter interposed between a stem and a head. The adapter includes a ball stud having a shank coupled to the stem and a ring coupled to the head. The ring has a spherical bearing surface which cooperates with a ball portion of the ball stud such that an angular adjusted between the ball stud and the ring may be effected. The ring is eccentrically coupled to the head such that relative angular positioning of the ring in the head will effect an adjustment in the radial offset.

The joint prosthesis system of the present teachings provides great flexibility in the adjustment of important bio-kinematic parameters for the prosthesis systems while minimizing the number of components required for the modular system.

Also provided according to the present teachings is a shoulder prosthesis comprising a stem having a first longitudinal axis. The shoulder prosthesis can also include an adaptor including a first taper. The first taper can have a first taper axis. The shoulder prosthesis can also include a plurality of indicia.

The shoulder prosthesis can include a head rotatably supported by the adaptor. The head can have a semi-spherical articulating surface. The head can be coupled to the first taper and can be positionable relative to the stem through rotation of the adaptor about the first taper axis for adjusting a radial offset of the head relative to the longitudinal axis of the stem. The plurality of indicia can indicate an alignment of the radial offset.

Further provided is a shoulder prosthesis comprising a stem having a longitudinal axis and a proximal face. The proximal face can define a bore. The shoulder prosthesis can include an adaptor having a first portion coupled to a second portion. At least a portion of the first portion can be received within the bore of the stem to couple the adaptor to the stem. The first portion can also have a first diameter. The second portion can have a second diameter different than the first diameter, and can define a first taper. The adaptor can also include a plurality of indicia. The shoulder prosthesis can include a head having a bottom face opposite a semispherical articulating surface. The bottom face can have a second taper that mates with the first taper of the second portion to couple the head to the adaptor. The rotation of the adaptor relative to the stem can adjust the radial offset of the head relative to the longitudinal axis of the stem. The plurality of indicia on the adaptor can indicate an alignment of the radial offset.

According to the present teachings, provided is a shoulder prosthesis comprising a stem having a longitudinal axis and a proximal face. The proximal face can define a bore. The shoulder prosthesis can include an adaptor having a first portion opposite a second portion. At least a portion of the first portion can be received within the bore of the stem to couple the adaptor to the stem. The first portion can have a first diameter and can be positioned about a first axis. The second portion can have a second diameter smaller than the first diameter. The second portion can define a first taper and can be positioned about a second axis. The second axis can be offset from the first axis. The adaptor can also include a plurality of indicia. The shoulder prosthesis can also include a head having a semispherical articulating surface and a bottom face opposite the semispherical articulating surface. The head can also include a third axis, which can be offset from the first axis and the second axis. The bottom face can have a second taper that mates with the first taper of the second portion to couple the head to the adaptor. The rotation of the adaptor relative to the stem can adjust the radial offset of the head relative to the longitudinal axis of the stem. The plurality of indicia on the adaptor can indicate an alignment of the radial offset.

A femoral prosthesis system according to various embodiments is disclosed. The system can include a femoral head having an articulating surface defining a diameter and a generally opposed surface, a head female taper formed into the femoral head through the opposed surface, wherein a head center axis of the femoral head is offset a first radial distance from a head taper center axis of the head female taper. The system can further include an adapter having a first side and a second generally opposed second side, the adapter further having an outer surface defining an adapter male taper and an adapter female taper formed into the adapter from the first side, wherein the adapter has an adapter center axis offset a radial distance from an adapter female taper axis. The system can also include a femoral stem having a body and a neck, wherein the neck extends at an angle relative to the body and the neck has an outer surface that defines a neck male taper. The femoral head, the adapter, and the neck are selectively connected to achieve a selected femoral head offset relative to the femoral stem.

A femoral prosthesis system according to various embodiments is disclosed. The system can include a femoral head sized and shaped for articulation with at least one of an acetabulum or an acetabular prosthesis. The femoral head can have an articulating surface defining more than a hemisphere and a diameter, an opposite surface generally opposed to the articulating surface, a head female taper formed into the femoral head through the opposite surface, and a head center axis of the femoral head is offset a first radial distance from a head taper center axis of the head female taper, wherein the head center axis is defined through a portion of the articulating surface defining an axis of motion with a pelvis of a patient. The system can further have an adapter having a first side and a second side generally opposed to the first side, the adapter further having an outer surface defining an adapter male taper and an adapter female taper formed into the adapter from the first side, wherein the adapter has an adapter center axis offset a radial distance from an adapter female taper axis. The system can also include a femoral stem having a body and a neck, wherein the neck extends at an angle relative to the body and the neck has an outer surface that defines a neck male taper. The femoral head, the adapter, and the neck can be selectively connected to achieve a selected femoral head offset relative to the femoral stem.

A method of implanting a femoral prosthesis system according to various embodiments is disclosed. The method can include determining an anteversion angle of a femur relative to a pelvis of the patient. The method can also include selecting an adapter having an adapter center axis and an adapter offset connection, wherein the adapter offset connection has an adapter connection center axis and selecting a femoral head having a head center axis and an offset head connection that has a head connection center axis. The selected adapter can be rotated relative to the selected femoral head to achieve a selected offset of the adapter connection center axis relative to the head connection center axis. The selected offset of the adapter connection center axis relative to the head connection center axis can be based on the determined anteversion angle.

Further areas of applicability will become apparent from the description provided herein. It should be understood that the description and specific examples are intended for purposes of illustration only and are not intended to limit the scope of the present teachings.

BRIEF DESCRIPTION OF THE DRAWINGS

The drawings described herein are for illustration purposes only and are not intended to limit the scope of the present teachings in any way.

FIG. 16B is a plan view of a variable femoral head in a third orientation;

FIG. 20 is an environmental view of a variable femoral prosthesis illustrating variable varus and valgus positions; and FIG. 21 is an environmental view of a variable femoral prosthesis illustrating variable anteversion and retroversion positions.

DETAILED DESCRIPTION

Figure 1:
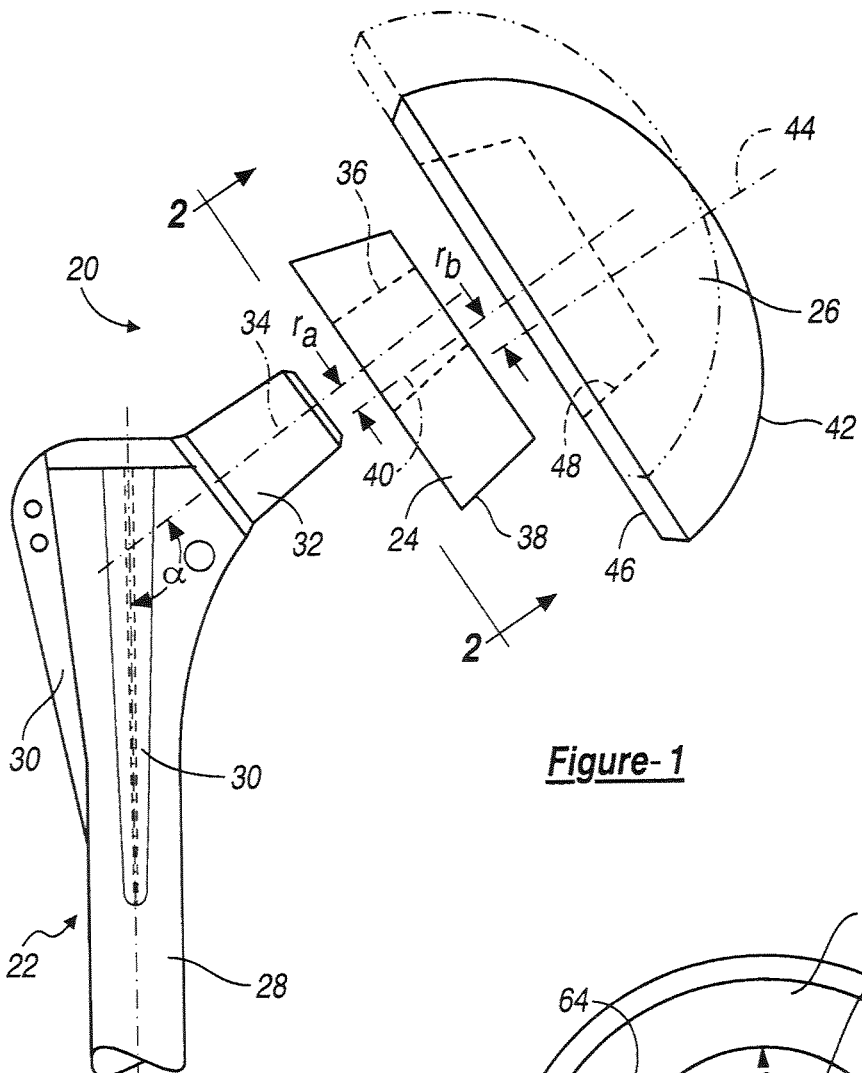
FIG. 1 is an exploded front view of a modular shoulder prosthesis system in accordance with the present teachings.

The following description is merely exemplary in nature and is not intended to limit the present teachings, application, or uses. It should be understood that throughout the drawings, corresponding reference numerals indicate like or corresponding parts and features. Although the following description is related generally to a modular joint prosthesis system which provides adjustment of the radial offset and/or angular inclination of the head relative to the stem, it will be understood that the system as described and claimed herein can be used in any appropriate surgical procedure. Thus, it will be understood that the following discussions are not intended to limit the scope of the present teachings and claims herein.

With reference now to FIG. 1, shoulder prosthesis 20 in accordance with the present teachings is illustrated to include a stem 22, an adapter 24 and a head 26. Stem 22 includes a rod portion 28 adapted to be received in the medullary canal of the humerus. A plurality of fins 30 are formed near the upper end of rod 28 for locating and fixing the stem within a humerus. A male taper 32 extends obtusely from rod 28 to provide a location for interconnecting stem 22 with adapter 24. Male taper 32 extends from stem 22 along axis 34. Stem 22 is of the type manufactured and sold by Biomet, Inc. as a component in its Bi-Angular® Shoulder System.

Adapter 24 is a generally cylindrical disc having a female taper 36 formed therein for receiving male taper 32 of stem 22. The outer surface 38 of adapter 24 defines a male taper. Female taper 36 is eccentrically located in adapter 24 such that central axis 34 of female taper 36 is not collinear with central axis 40 of adapter 24. Instead, central axis 40 is radially offset from central axis 34 by an amount indicated as $r_a$.

Head 26 includes a semispherical surface 42 defined about central axis 44. Bottom face 46 is formed opposite semi-spherical surface 42 and has a female taper 48 formed therein which is configured to receive adapter 24 along central axis 40. In this regard, female taper 48 is formed eccentrically within head 26 such that a radial offset $r_b$ exists between central axis 40 and central axis 44.

Figure 2:
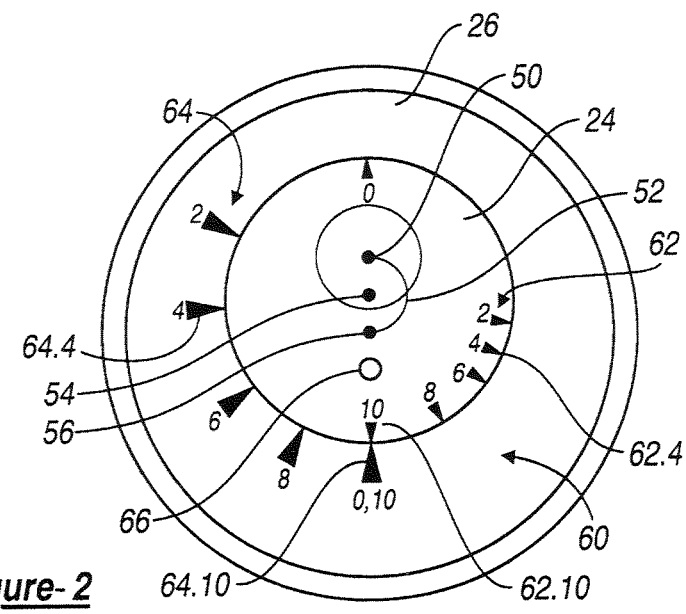
FIG. 2 is a normal view of the adapter and head components of the device illustrated in FIG. 1 shown in an assembled state.

As previously described, the eccentric relationship of central axes 34, 40 and 44 provide an arrangement whereby a relative rotational positioning of adapter 24 with respect to head 26 adjusts the radial offset within a given range. As best seen in FIG. 2, relative positioning of adapter 24 within female taper 48 of head 26 causes centroid 50 defined by female taper 36 to trace a helical path 52 relative to centroid 54 defined by central axis 40. Helical path 62 terminates at centroid 56 defined by central axis 34. A maximum radial offset is achieved when centroid 50 is located directly opposite centroid 56. Similarly, a minimum offset is achieved when centroid 50 aligns with centroid 56. In one example, the maximum radial offset is 10 mm and the minimum radial offset is 0 mm. However, one skilled in the art will recognize that the range of offset may be modified based on the design criteria for a given modular prosthesis system.

With continuing reference to FIG. 2, the shoulder prosthesis 20 is provided with indicia 64 facilitating adjustment and alignment of the radial offset. Specifically indicia 60 includes a first set of indicators 62 formed on adapter 24 and a second set of indicators 64 formed on bottom face 46 of head 26. First and second indicators 62, 64 have a magnitude value associated therewith indicating the amount of radial offset. Furthermore, head indicators 64 include an enlarged arrowhead which indicate the direction of the radial offset. In this manner, indicia 60 provide a radial offset vector which may be utilized to precisely align adapter 24 and head 26 and achieve the desired radial offset.

For example, as shown in FIG. 2, adapter indictor 62.10 associated with a 10 millimeter offset is aligned with head indictor 64.10 associated with 0,10 offset. Thus, the relative angular position of adapter 24 with respect to head 26 shown in FIG. 2 provides a 10 millimeter offset and the direction of the offset is indicated by arrowhead 64.10. The radial offset may be reduced by removing adapter 24 from head 26, rotating adapter 24 until indicia 60 are properly aligned and inserting adapter 24 into female taper 48 of head 26. For example, an offset of 4 millimeters would be obtained by aligning adapter indictor 62.4 with head indictors 64.4 at which point a 4 millimeter offset in the direction of arrowhead 64.4 would be achieved. In one example, a threaded through bore 66 may be formed in adapter 24 for receiving a threaded member to facilitate a disassembly of adapter 24 from head 26. In certain applications, a removeable plug (not shown) in the form of a bio-compatible cement or the like may be disposed in bore 66 to minimize joint fluid from entering the interface between the adapter 24 and the head 26 through the bore 66.

Figure 3:
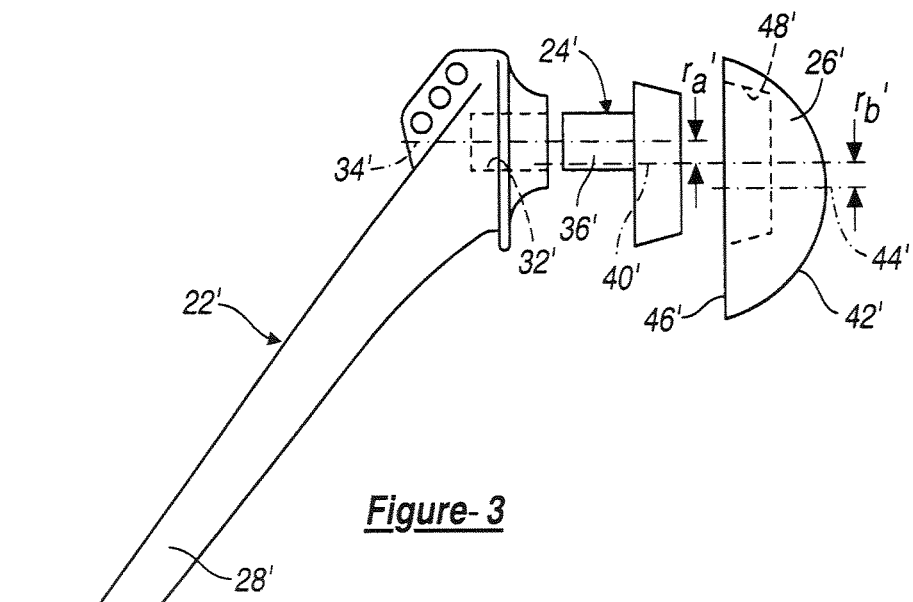
FIG. 3 is an exploded front view of an alternate embodiment of the modular shoulder prosthesis system illustrated in FIG. 1.
Figure 4:
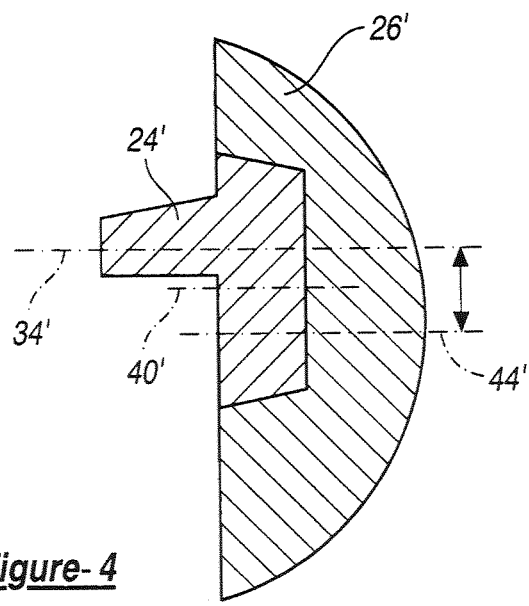
FIG. 4 is a cross-sectional view of the adapter and head shown in FIG. 3 arranged to provide a maximum radial offset.
Figure 5:
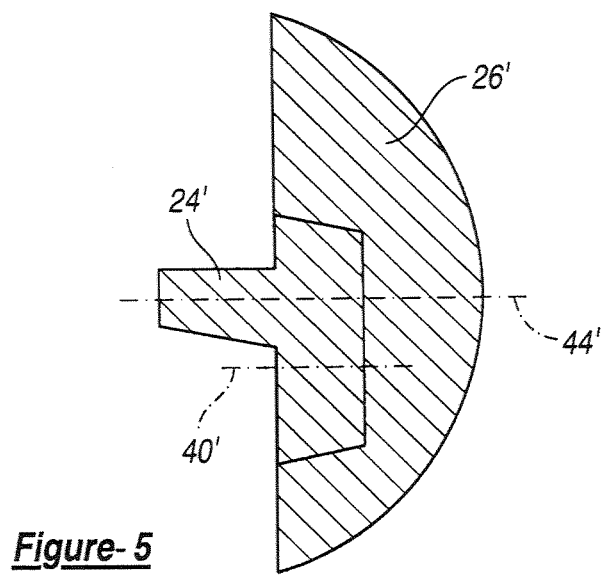
FIG. 5 is a cross-sectional view of the adapter and head shown in FIG. 4 and arranged to provide a minimum radial offset.

With reference now to FIGS. 3 through 5, an alternate embodiment of the present teachings is illustrated in which the adapter has a first male taper adapted to engage the stem and a second male taper adapted to engage the head. With reference now to FIG. 3, stem 22' includes a rod portion 28' and a female taper 32' formed in the end opposite rod 28' which defines central axis 34'. Stem 22' is of the type manufactured and sold by Biomet as a component of its Bio-Modular® Shoulder System. Adapter 24' has a first male taper 36' adapted to be inserted into female taper 32' and a second male taper 38' formed along central axis 40'. Head 26 includes a semispherical surface 42' defined about central axis 44'. Bottom face 46' has a female taper 48' formed therein which is adapted to receive male taper 38' of adapter 24'. Central axis 40' is offset from central axis 34' as indicated at $r_a'$ and central axis 44' is offset from central axis 40' as indicated at $r_b'$. As in the first embodiment, relative rotational positioning of adapter 24' and head 26' provides an adjustable radial offset for shoulder prosthesis 20'.

With reference now to FIG. 4, central axis 34' of male taper 36' is located directly opposite central axis 44' of head 26' to provide a maximum radial offset. With reference now to FIG. 5, head 26' has been rotated 180 degrees relative to adapter 24' such that central axis 44' is collinear with central axis 34'. In this orientation, a minimum radial offset is provided. Indicia similar to that described above with reference to FIG. 2 facilitates alignment of shoulder prosthesis 20'.

Based on the foregoing detailed description, one skilled in the art will readily recognize that one aspect of the present teachings is directed to an adapter and head having eccentric configurations such that a relative rotation therebetween provides an adjustable range of offset configuration.

With reference now to FIGS. 6 through 10, a second alternative embodiment of the present teachings is illustrated which provides for adjustment of the angular inclination between the stem component and the head component in a manner similar to that described with reference to the radial offset. Specially, the shoulder prosthesis system 120 of the second alternative embodiment includes a stem 122, a head 124 having a first angular orientation and an adapter 126 interconnecting the stem 122 and the head 124 such that the adapter 126 has a second angular inclination. The adapter 124 is configured to be rotatably positionable with respect to the head 126 such that the angular inclination of the head 126 relative to the stem 122 may be adjusted.

Figure 6:
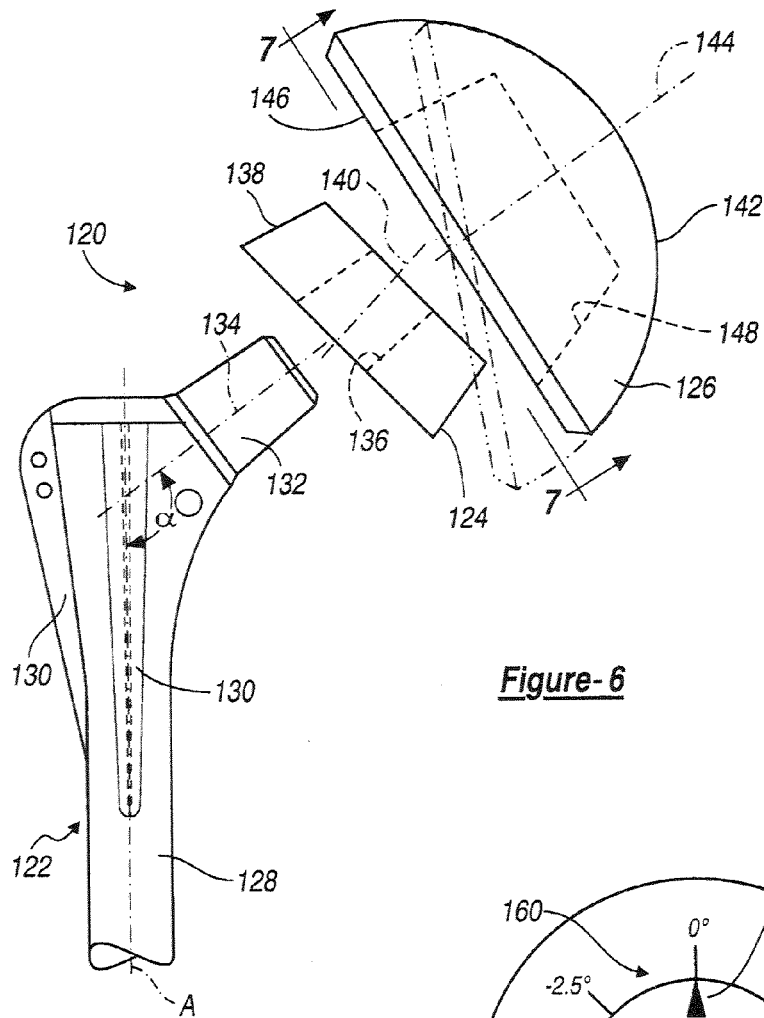
FIG. 6 is an exploded front view of a second alternative embodiment of a modular shoulder prosthesis system according to the present teachings.

With specific reference to FIG. 6, shoulder prosthesis 120 includes stem 122 having rod 128 extending therefrom. A plurality of fins 130 are formed longitudinally along rod 128 parallel to central longitudinal axis A near the upper end of stem 122. A male taper 132 extends from rod 128 at an obtuse angle α with respect to the central longitudinal axis A and defines a central axis 134.

Adapter 124 is a generally cylindrical disc having a female taper 136 formed therein. The outer surface of adapter 124 defines a male taper 138. The central axis 140 of adapter 124 is configured at a first angular orientation with respect to central axis 134. Specifically, central axis 140 is defined by the angle at which female taper 130 is oriented relative to the bottom surface 125 of adapter 124. In one example, central axis 140 is disposed at a +5 degree angular inclination with respect to central axis 134.

Head 126 includes a semispherical surface 142 and a flat bottom face 146 having a female taper 148 formed therein. Female taper 148 defines central axis 144 which is disposed at an angular inclination relative to a central axis 140. Specifically, central axis 144 is defined by the angle at which female taper 144 is oriented relative to bottom face 146. In one example, central axis 144 is disposed at a −5 degree angular inclination with respect to central axis 140.

The relative rotational position of adapter 124 with respect to the head 126 defines the adjustment to the prosthesis inclination relative to central axis 34. For example, as illustrated in FIG. 6, adapter 126 provides a +5 degree inclination which is canceled by the −5 inclination provided in head 126. Thus, when adapter 124 and head 126 are assembled a net zero angular inclination is achieved. An angular adjustment may be provided by rotating adapter 124 relative to head 126 such that a net angular inclination is provided. For example, when adapter 124 is rotated clockwise 90 degrees, the angular inclination of central axis 140 combines with the angular inclination of central axis 144 to provide a +5 degree angular inclination of head 126 relative to central axis 134. Likewise, an additional 90 degree rotation of adapter 124 will provide an overall adjustment of +10 degrees in the angular inclination. In one example, a range of angular inclination is provided between 0° and 10°. However, one skilled in the art will recognize that the range of angular inclination may be modified based on the design criteria for a given modular prosthesis system.

Figure 7:
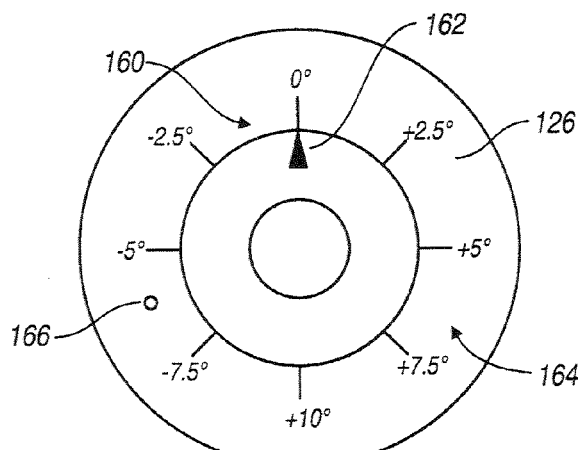
FIG. 7 is a normal view of the adapter and head illustrated in FIG. 6 shown in an assembled state.

With continuing reference to FIG. 7, adapter 124 and head 126 are provided with inclination indicia 160 which facilitates identification of the magnitude and direction of the angular inclination provided by shoulder prosthesis system 120. Specifically, angular indicia 160 includes a first indictor 162 on adapter 124 and a plurality of second indicators 164 provided on bottom face 146 of head 126. Adapter indicator 162 is an arrowhead which indicates the direction of the angular inclination. Head indicators 164 provide a magnitude of angular inclination as well as an alignment mark which cooperates with adapter indictor 162 to provide the angular inclination vector (i.e. magnitude and direction).

Figure 8:
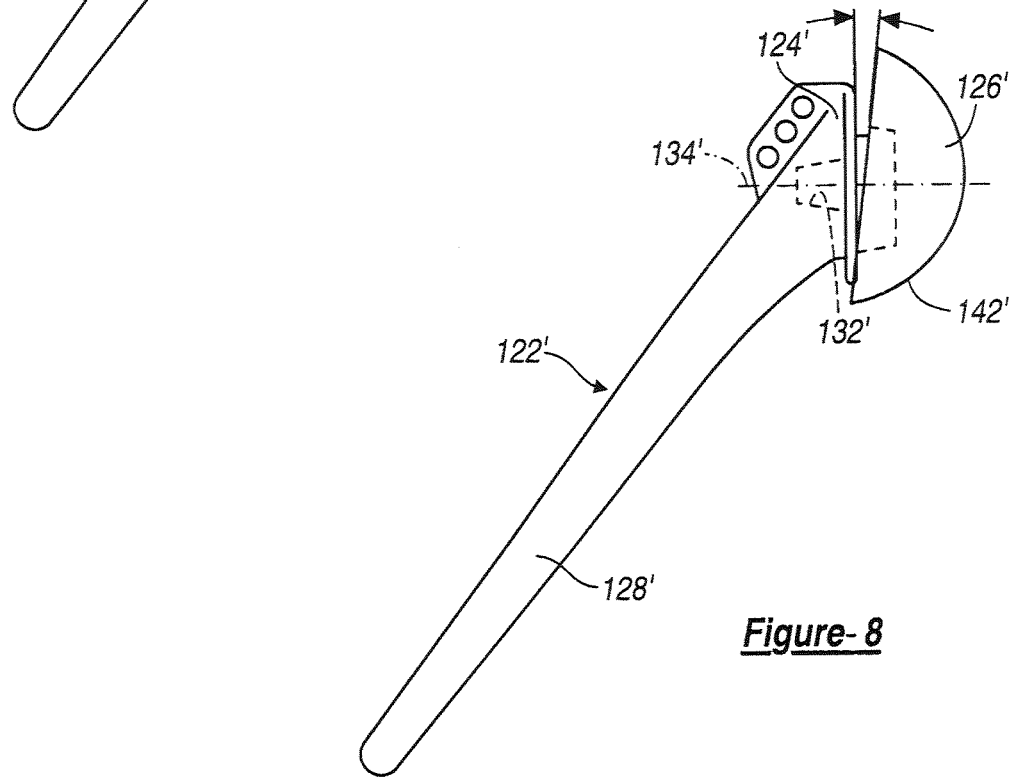
FIG. 8 is an alternate embodiment of the modular shoulder prosthesis system illustrated in FIG. 6.
Figure 9:
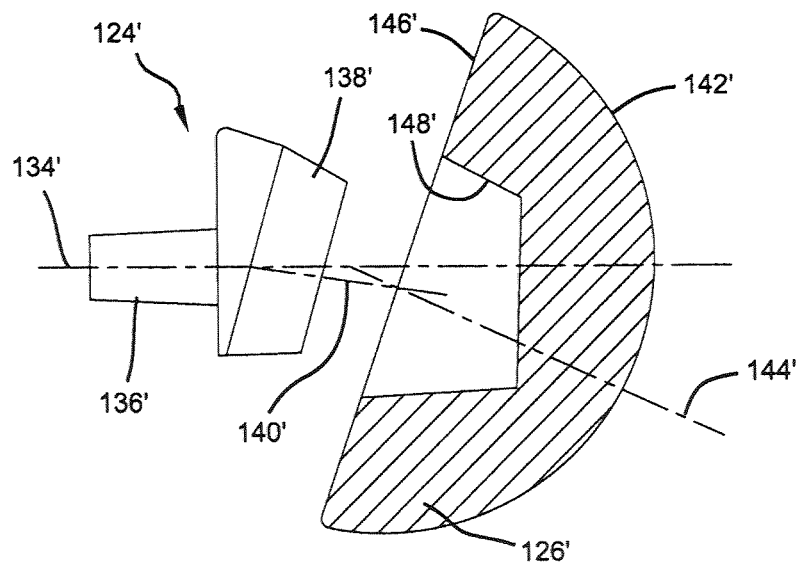
FIG. 9 is a partial cross-sectional view showing the adapter and head of FIG. 8 arranged to provide a maximum angular inclination.
Figure 10:
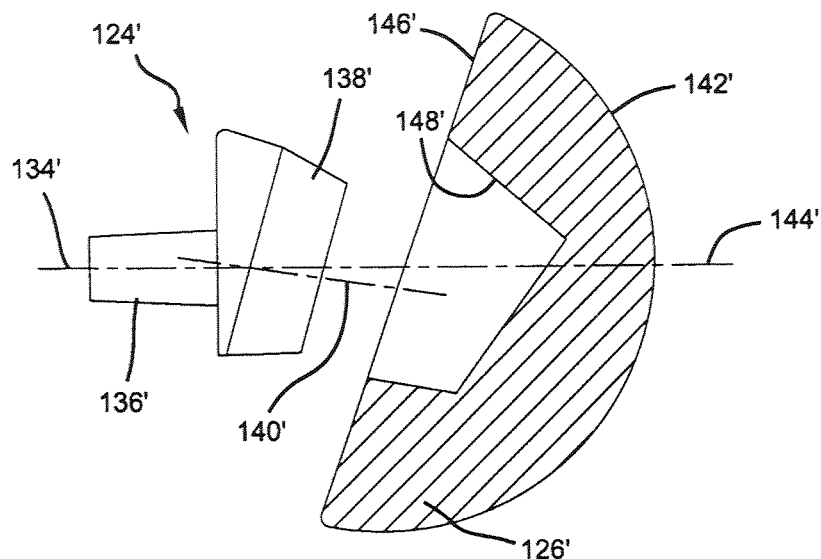
FIG. 10 is an illustration of the adapter and head similar to that shown in FIG. 9 and arranged to provide a minimum angular inclination.

With reference now to FIGS. 8 through 10, an alternate embodiment to the second alternative embodiment is illustrated in which the adapter has a first male taper adapted to engage the stem and a second male taper adapted to engage the head. With reference now to FIG. 8, stem 122' includes a rod portion 128' and a female taper 132' formed in the end opposite rod 128' which defines central axis 134'. Adapter 124' has a first male taper 136' adapted to be inserted into female taper 132' and a second male taper 138' formed along central axis 140'. Head 126' includes a semispherical surface 142' defined about central axis 144'. Bottom face 146' has a female taper 148' formed therein which is adapted to receive male taper 138' of adapter 124'. Central axis 140' is angularly inclined relative to central axis 34' and central axis 144' is angularly inclined relative to central axis 140'. Relative rotational positioning of adapter 124' and head 126' provides an adjustable angular inclination for shoulder prosthesis 120'.

With reference now to FIG. 9, the angular inclination of central axis 134' of male taper 136' is complementary with the central axis 144' of head 26' to provide a maximum angular inclination. With reference now to FIG. 10, head 126' has been rotated 180 degrees relative to adapter 124 such that the angular inclination of central axis 144' is opposing central axis 134' to provide a minimum angular inclination.

From the foregoing description of various embodiments, one skilled in the art will readily recognize that the present teachings are directed to a modular shoulder prosthesis in which the radial offset and/or the angular inclination (i.e. inversion and retroversion) of the head relative to the stem may be adjusted by relative rotational positioning of an adapter interdisposed between the stem and head components of the shoulder prosthesis. In this way, a range of radial offsets and/or angular inclinations may be provided without requiring numerous additional components. The various embodiments have discussed a radial offset adjustment or an angular inclination adjustment independently; however, one skilled in the art will readily recognize that a shoulder prosthesis system may incorporate both aspects of a radial and angular adjustment. Where a single adapter utilized to interconnect the stem and the head, an interrelationship exists between the radially offset adjustment and the angular inclination adjustment. In combination, a system could be employed which utilized two intermediate adapters such that the radial offset and angular inclination adjustment are isolated and thus independent. For example, the interface between a first adapter and a second adapter would provide the desired radial adjustment as described in particular reference to the first embodiment and the interface between the second adapter and the head would provide the angular inclination as described with reference to the second alternative embodiment. In such a system, each of the radial offset and angular inclination adjustments would be provided by a single interface, thereby minimizing the interrelation between both adjustments resulting from a single intermediate adapter.

Figure 11:
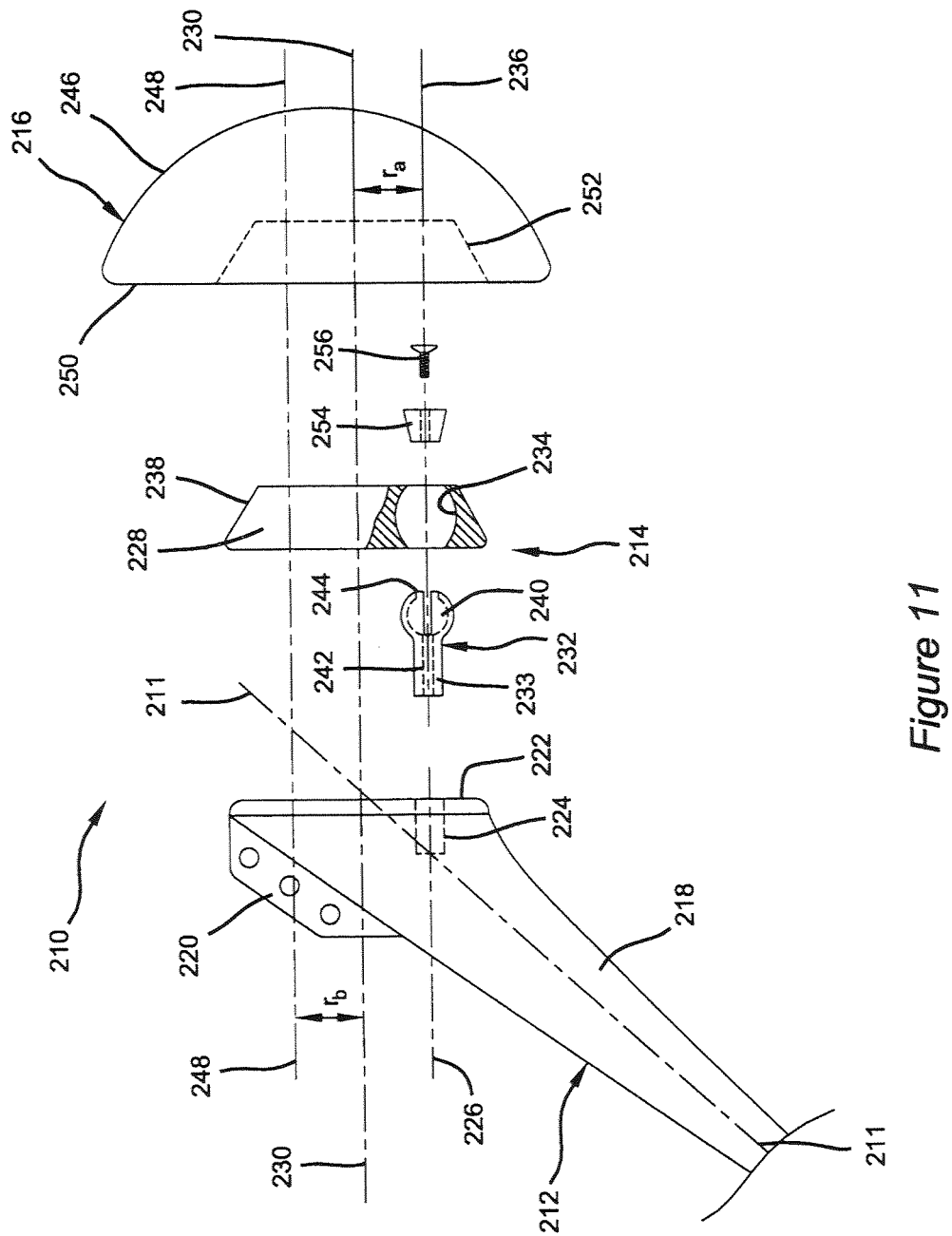
FIG. 11 is an exploded front view of a third alternative embodiment of a modular shoulder prosthesis system according to the present teachings.
Figure 12:
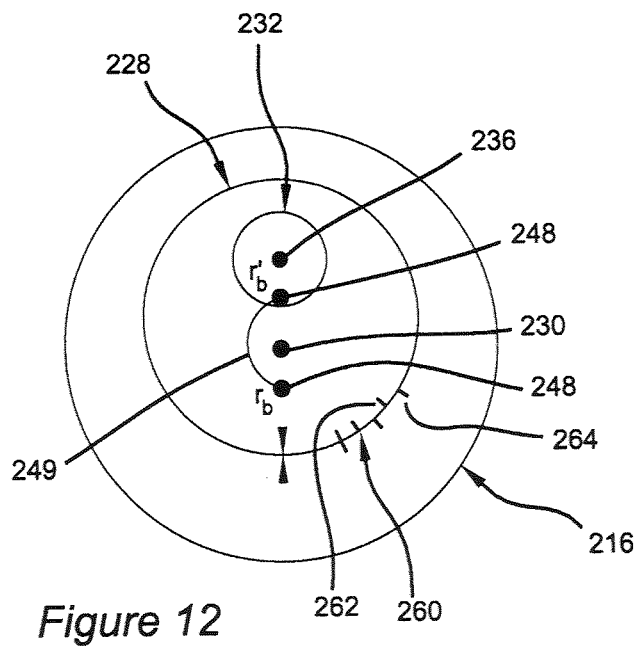
FIG. 12 is a normal view of the adaptor and head components of the device shown in FIG. 11 oriented in a first position.
Figure 13:
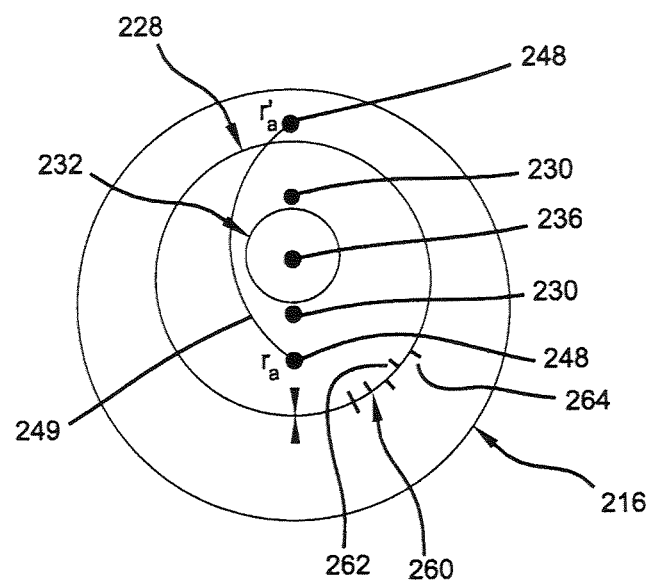
FIG. 13 is a normal view similar to FIG. 12 with the components oriented in a second position.

With reference now to FIGS. 11-13, a third alternative embodiment of the present teachings is illustrated which provides for adjustment of both the radial offset and the angular inclination. Specifically, the shoulder prosthesis 210 is provided and includes a stem 212, an adaptor 214 and a head 216. The stem 212 includes a longitudinal axis A along its length and further includes a rod portion 218 adapted to be received into the medullary canal of the humerus. A plurality of fins 220 are formed near the proximal end of the rod 218 for locating and fixing the stem 212 within the humerus whereby the proximal end of the rod 218 has a substantially larger body than that of the distal end and includes a proximal face 222 having a bore 224 formed therein along a central axis 226 for receiving the adaptor 214. The proximal face 222 extends from the stem 212 along axis 226 and provides a location for interconnecting the stem 212 with the adaptor 214. Further, the proximal face 222 provides sufficient clearance for angular and radial adjustments of the adaptor 214 and the head 216 as will be discussed in more detail below.

The adaptor 214 is a generally cylindrical member including an outer ring 228 having a central axis 230 and a ball stud 232 rotatably connected to the ring 228. The ring 228 includes an attachment aperture 234 having a central axis 236 formed therethrough for rotatable engagement with the ball stud 232. The ring 228 further includes an outer surface having a male taper 238 for engagement with the head 216.

The ball stud 232 includes a shank segment 233 for engagement with the bore 224 of the stem 212 and a divided ball segment 240 for attachment to attachment aperture 234 of the ring 228. The ball stud 232 further includes a second bore 242 formed therein for interaction with a fastener 244 for selectively securing the ring 228 to the ball stud 232 in a fixed orientation. Fastener 244 includes a wedge portion 254 and a set screw 256 as best shown in FIG. 11. Set screw 256 is received by a central bore of the wedge 254, whereby as the set screw 256 is driven into the wedge 254, the wedge 254 expands within the attachment aperture 234 of the ring 228 thereby securing the ring 228 and ball stud 232 in a fixed relationship. In this regard, the central axis 236 of the ball stud 232 is concentric with central axis 226 of the proximal face 222 and is received by the attachment aperture 234 such that the central axis 236 of the ball stud 232 is eccentric to the central axis 230 of the ring 228 as indicated by $r_a$.

The head 216 is rotatably supported by the adaptor 214 and includes a semispherical surface 246 defined about a central axis 248 adapted for mating engagement with the glenoid cavity of a scapula. The head 216 further includes a bottom surface 250 formed opposite the semispherical surface 246 having a female taper 252 for mating engagement with the male taper 238 of the ring 228. In this regard, the female taper 252 is received eccentrically within the head 216 such that a radial offset $r_b$ exists between the central axis 230 of the ring 228 and the central axis 248 of the head 216. While the present teachings disclose a head 216 for mating engagement with the glenoid cavity of a scapula, it is anticipated that the head 216 could also be received by a prosthetic device replacing a severely damaged glenoid cavity and should be considered within the scope of the present teachings.

As previously described, the eccentric relationship of the central axes 230, 236 and 248 provides an arrangement whereby a relative rotational positioning of the adaptor 214 with respect to the head 216 or a relative rotational positioning of the adaptor 214 with respect to the ball stud 232 or a combination thereof adjusts the radial offset of the head 216 relative to the longitudinal axis A of the stem 212.

With particular reference to FIG. 13, relative positioning of the head 216 to the longitudinal axis A of the stem 212 is accomplished by a first radial adjustment method. In the first radial adjustment method, the relative positioning of the ring 228 within the female taper 252 of the head 216 causes the central axis 248 of the head 216 to be rotated relative to the central axis 230 of the ring 228. The radial offset between the central axis 248 and the central axis 230 is again denoted by $r_b$ at its minimum and by $r_b'$ at its maximum value. FIG. 12 further traces the movement of axis 248 from $r_b$ to $r_b'$ as indicated by path 249, while each position along path 249 signifies a potential adjustment of the head 216 relative to the longitudinal axis A of the stem 212.

With particular reference to FIGS. 12 and 13, relative positioning of the head 216 to the longitudinal axis A of the stem 212 is accomplished by a second radial adjustment method. In the second radial adjustment method, the relative positioning of the central axis 230 of the ring 228 and the central axis 236 of the ball stud 232 causes the central axis 248 of the head 216 to be rotated. Again, $r_a$ is used to designate the minimum offset between the central axis 230 of the ring 228 and the central axis 236 of the ball stud 232 while $r_a'$ is used to designate the maximum offset. FIG. 13 further traces the movement of axis 248 from $r_a$ to $r_a'$ as indicated by path 251, while each position along path 251 signifies a potential adjustment of the head 216 relative to the longitudinal axis A of the stem 212. For discussion purposes, the head 216 does not rotate relative to the ring 228 when making an adjustment of the ball stud 232 relative to the ring 228, but it should be understood that both adjustment methods could be used concurrently to achieve an overall desired radial offset of the head 216 relative to the longitudinal axis A of the stem 212.

In addition to providing a radial offset, the shoulder prosthesis 210 further provides an angular adjustment of the head 216 relative to the longitudinal axis A of the stem 212 for both inversion and retroversion adjustments. As best shown in FIG. 13, the central axis 248 of the head 216 rotates about the central axis 236 of the ball stud 232, which is concentric with the central axis 226 of the first bore 224. As previously discussed, the divided ball segment 240 of the ball stud 232 rotatably supports the ring 228 while the ring 228 supports the head 216. By articulating either the head 216 or the ring 228, the ring 228 will rotate on the divided ball segment 240 of the ball stud 232, thereby providing the head 216 with an angular adjustment relative to the longitudinal axis A of the stem 212. For discussion purposes, the first and second radial adjustment methods are not utilized while making an angular adjustment of the head 216, however, it should be understood that both adjustment methods may be used concurrently with the angular adjustment method and with one another to achieve an overall desired angular and radial relationship of the head 216 relative to the longitudinal axis A of the stem 212.

With continuing reference to FIGS. 12 and 13, the shoulder prosthesis is provided with indicia 260 facilitating adjustment and alignment of the radial offset. Specifically, indicia 260 includes a first set of indicators 262 formed on the ring 228 and a second set of indicators 264 formed on the bottom face 250 of the head 216. First and second indicators 262, 264 have a magnitude value associated therewith indicating the amount of radial offset. Furthermore, the head indicators 264 include an enlarged arrowhead which indicates the direction of the radial offset. In this manner, indicia 260 provide a radial offset vector which may be utilized to precisely align the adaptor 214 and the head 216 and achieve the desired radial offset.

Figure 14:
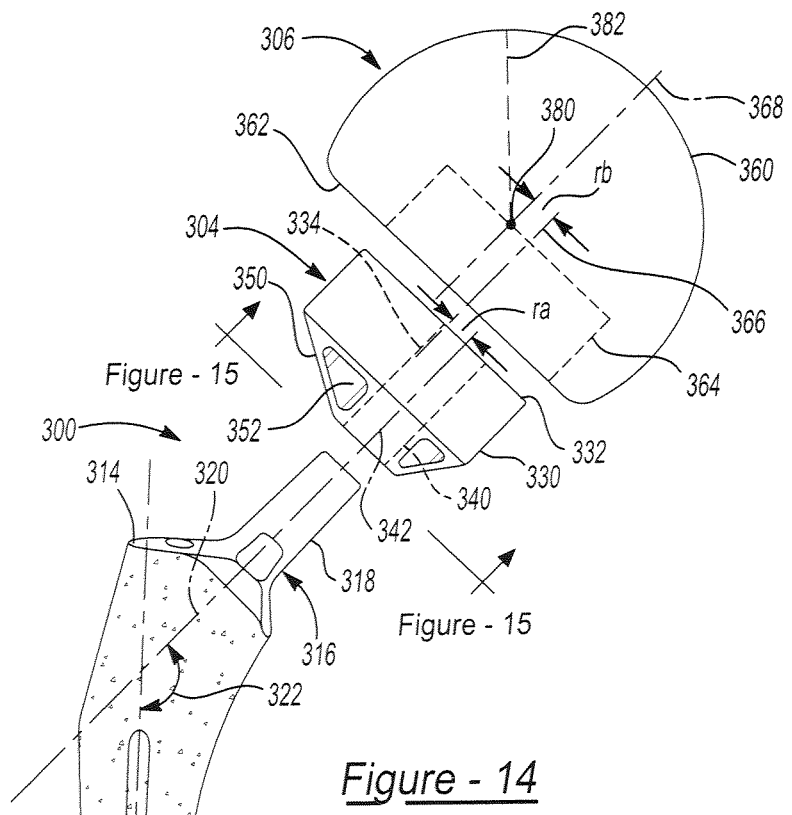
FIG. 14 is an exploded plan view of a variable femoral prosthesis, according to various embodiments.
Figure 19:
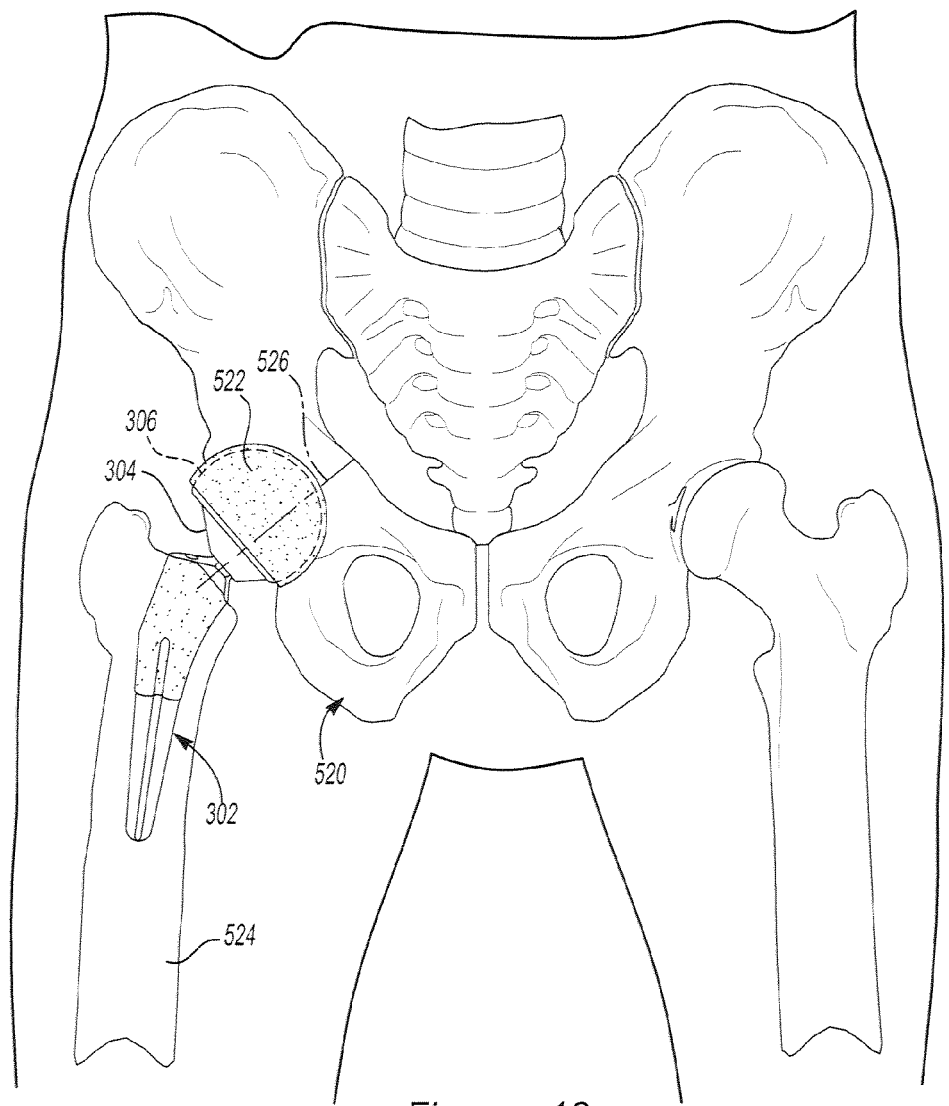
FIG. 19 is an environmental view of an implanted variable hip prosthesis.

Disclosed above is a prosthesis that can be used in various embodiments to repair a proximal portion of a humerus. The prosthesis, according to various embodiments, can also be used to repair or replace a proximal portion of a femur 522 (FIG. 19). A variable femur prosthesis 300 is illustrated in FIG. 14. The variable femoral prosthesis 300 can include portions similar to the prosthesis illustrated in FIG. 1 as described further herein. For example, the variable femoral prosthesis 300 can include a stem 302, an adapter 304, and a femoral head 306. Each of the stem 302, the adapter 304, and the femoral head 306 can be similar to prosthetic portions, such as those described above, but formed to replace a proximal femoral portion. In addition, the various portions of the femoral prosthesis 300 can be similar to those commercially available, such as the Femoral Prosthesis sold as the Magnum™ Femoral Prosthesis sold by Biomet. Inc.

The stem 302 can include a rod portion 310 that is formed to be positioned within a femoral canal that can be reamed or formed within a femur, as illustrated in FIG. 19. The rod 310 can extend along an axis 312 and can terminate at an upper edge 314 that can be positioned near a proximal portion of the femur. A neck 316 can extend from a proximal portion or terminal end of the rod 310. The neck 316 can include an external surface that defines a male taper 318. The neck 316 can extend along an axis 320. The neck axis 320 and the rod axis 312 can form an angle 322 relative to one another. The angle 322 can generally be an obtuse angle.

The adapter 304 can be formed to include an external surface 330 that defines a male taper. The adapter 304 can also terminate in a surface 332. A central axis 334 can be an axis that is defined through a center of the male taper 330 or the end surface 332. A female taper 340 can also be defined by a depression or bore of the adapter 304. The female taper 340 can define a central axis 342 that is eccentric or offset by a radial offset $r_a$. The radial offset $r_a$ can be about 0.1 millimeters (mm) to about 10 mm, and further can be about 0.1 mm to about 5 mm, and can further be about 3 mm to about 5 mm, inclusive. Accordingly, the radial offset $r_a$ of the adapter 304 can allow the adapter 304 to have an edge that is positioned a greater distance from the neck 316 that another edge, as discussed further herein.

The adapter 304 can further include a further tapered surface or stem facing taper surface 350 that can assist in providing clearance around the neck 316 relative to the femoral stem 302. Additionally, depressions, such as a depression 352 can assist in inserting or engaging the adapter 304 into the head 306. It will be further understood, however, that the adapter 304 can include a threaded aperture similar to the threaded aperture 66 discussed above for removal of the adapter 304 from the head 306.

The femoral head 306 can be formed to have an exterior articulating surface 360 that is substantially smooth or otherwise provided to articulate with a portion of either an acetabular prosthesis or a natural acetabulum of a patient. The exterior surface 360 of the femoral head 306 can define any selected portion of a sphere. For example, the exterior surface 360 can define a hemisphere or more than a hemisphere. The femoral head 306 can also include a stem facing surface 362 into which the articulating surface 360 terminate. The stem facing surface 360 can be substantially flat or in an appropriate configuration to allow for clearance of the anatomy relative to the femoral head 306.

Formed into the femoral head 306 through the stem facing surface 362 can be a female taper 364. The female taper 364 can define a taper axis 366 that is generally defined through a center of the female taper 364. The femoral head 306 can define a head middle axis 368 that is generally defined through a center of the femoral head 306. The taper axis 366 and the head axis 368 can be offset from one another radially by a radial offset $r_b$. The head radial offset $r_b$ can be any appropriate offset, such as within the range discussed above. For example, the head radial offset $r_b$ can be about 0.1 mm to about 10 mm, further can be about 0.1 mm to about 5 mm, and can further be about 3 mm to about 5 mm, inclusive. Accordingly, the femoral head 306 can include an external edge or surface that extends beyond or is positioned away from a portion of the neck 316 in a first direction and a lesser distance away from the neck 316 in another direction.

As discussed above and further herein, the male taper 318, the female taper 340, the male taper 330, and the female taper 364, can be formed of any appropriate taper dimension. For example, a morse type taper or other self locking taper configurations can be provided. Self locking tapers generally have complimentary angles of about 3-5 degrees. Accordingly, the male taper can have an external taper angle of about 3-5 degrees from a central axis while the female taper can have an internal complimentary taper of about 3-5 degrees central axis of the female taper. The taper dimensions can allow for a sufficiently locking configuration or fixed configuration between the female and female tapers when interconnected.

The femoral head 306 can be generally spherical and include a center 380 where a radius extends from the center 380 to the surface 360 of the femoral head 306. The radius 382 can be any appropriate size, such as about 10 millimeters (mm) to about 50 mm, including about 10 mm to about 35 mm, and further including about 11 to about 11 mm. The femoral head 306 can define a portion of a sphere generally to the flat or rear side 362. The portion of the sphere defined by the femoral head 306 can be an appropriate mount such as about 50% to about 95%, about 55% to about 90%, and further including about 60% to about 80%. Accordingly, the femoral head 306 can define more than a hemisphere of a sphere. The articulating surface 360 can be provided to articulate for a selected range of motion with the acetabular prosthesis or acetabulum of the patient with a greater portion of the sphere defined by the femoral head 306.

Figure 15:
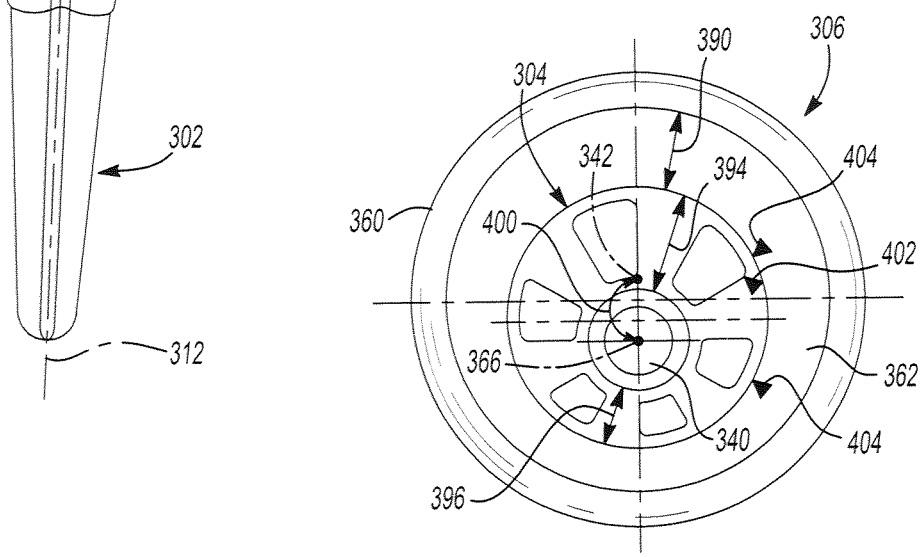
FIG. 15 is a plan view along line FIG. 15-FIG. 15 of FIG. 14.

With reference to FIG. 15, a view from plane FIG. 15 in FIG. 14 is illustrated. Generally, the rear surface 362 of the femoral head 306 is illustrated. The femoral head 306 defines the female taper 364 discussed above. Positioned within the female taper is the adapter 304. As illustrated in FIG. 15, the adapter 304, when positioned within the female taper 364 defined by the femoral head 306, is offset by the radial offset $r_b$ such that a first distance 390 is defined from one edge of the adapter 304 to a first edge of the stem facing side 362 and a second distance 392 is defined between the adapter 304 and a second edge of the stem facing side 362. The first distance 390 can differ from the second distance 392. The radial offset $r_b$, therefore, positions the adapter 304 in a non-central or off center axis location within the femoral head 306. Additionally, the female taper 340 of the adapter 304 is offset a first distance 394 from a first edge of the adapter in a second distance 396 from a second side of the adapter 304. The first distance 394 and the second distance 396 can differ. Accordingly, the female taper 340 includes the radial offset $r_a$ within the adapter 304.

It is further understood that the male and female tapers in the respective femoral head 306 and adapter 304 can be reversed. Similarly, the male taper 318 of the neck 316 and the female taper 340 of the adapter can be reversed. Thus, although respective axes of the male and female tapers can be maintained at radial offset positions, as discussed above, the taper connections can be reversed in selected embodiments.

The female taper 340 can be offset from the center axis 366, as illustrated in FIG. 15. The adapter 304, however, can be rotated within the female taper 364 within the femoral head 306. Accordingly, the center 342 of the female taper 340 in the adapter 304 can move along an ellipsis 400 by rotating the adapter 304 relative to the femoral head 306.

The ellipsis 400 can be similar to the ellipsis 52 discussed above relative to the prosthesis 26. Accordingly, the center 342 of the female taper 340 of the adapter 304 can be moved relative to the center 366 of the femoral head 306. The amount of offset from the center 366 of the femoral head 306 can be defined by the amount of rotation of the adapter 304 relative to the femoral head 306. The amount of rotation can be indicated by a first marking 402 on the adapter 304 and one or more markings 404 positioned on the stem facing side 362 of the femoral head 306. The adapter marking 402 can be similar to the markings 62 discussed in FIG. 2. The femoral head marking 404 can also be similar to the prosthesis markings 64 discussed in FIG. 2. Accordingly, the amount of offset that will be achieved by positioning the adapter 304 at a selected rotational position within the femoral head 306 can be determined by matching the indications 402 on the adapter 304 with markings 404 on the femoral head 306 and referring to the result. Appropriate markings can be provided to indicate an amount of change at about 1 degree changes and/or about 2 degree markings. Generally, a maximum amount of anteversion angle change markings can include about five degrees to about 10 degrees. Similarly, the markings can show varus and valgus position and rotation or selection of position of the head can be used to achieve a selected varus and valgus offset.

As discussed further herein, the radial offset $r_b$ of the femoral head 306 and the radial offset $r_a$ of the adapter 304 can be used to compensate for or achieve a selected amount of anteversion or angle offset required due to acetabular prosthesis placement in or natural acetabular anatomy of a patient. For example, an anteversion of a patient can be about five degrees to about 10 degrees. A prosthesis, however, positioned within a femur is positioned at a selected orientation and must articulate with the acetabulum or an acetabular prosthesis in an appropriate manner. If a femoral prosthesis is positioned within the femur at an orientation that does not allow for an achievement of a selected anteversion, the adapter 304 can be rotated to a selected position relative to the femoral head 306 to allow for the femoral head 306 to be positioned at a selected orientation relative to the remaining anatomy of the patient when connected to the neck 316. The head 306 and adapter 304 can, therefore, achieve a range of offset angles between the femur and the pelvis. Accordingly, the adapter 304 and the femoral head 306 can be provided to minimize inventory of selected femoral heads, femoral stem prosthesis to be positioned of the femur. Also, the range of offsets can allow for a selected orientation of the femoral prosthesis to be placed in the femur bone of the patient to maintain a selected bone mass relative to the femoral prosthesis. Moreover, an offset can be selected to compensate for less than optimal femoral stem 302 placement or acetabular prosthesis placement.

With continuing reference to FIG. 15 and addition reference to FIGS. 16A, 16B, 16C, and 17, exemplarily placements of the adapter 304 relative to the femoral head 306 are illustrated. With initial reference to FIG. 16A, the femoral head 306 includes or defines the center head axis 368, as discussed above. The female taper 340 and the adapter 304 defines the middle axis of the taper 342. When rotated to a selected position and the adapter 304 is positioned in the femoral head 306, a selected offset of 410 can be achieved. The offset of 410 can be a maximum offset of the center of the female taper 342 relative to the center of the femoral head 368. The maximum offset 410 can be any appropriate amount such as about one mm to about 20 mm, including about two mm to about 15 mm, and further including about 2 mm to about 10 mm. The amount of offset can be selectively achieved, by rotating the adapter 304, as discussed in relation to FIG. 15.

Figure 16A:
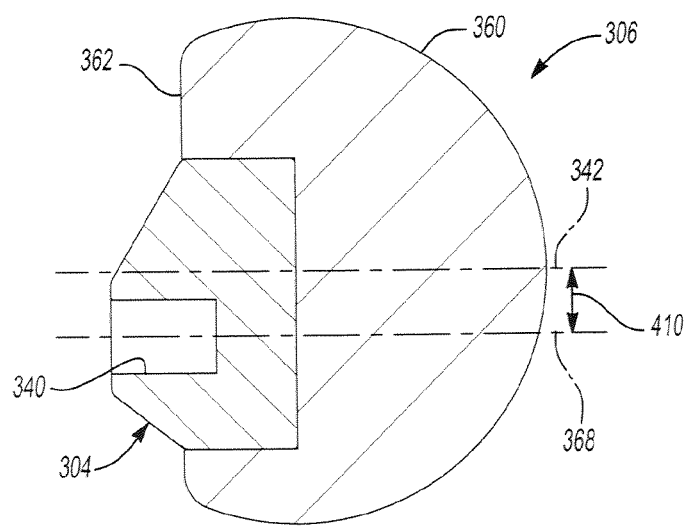
FIG. 16A is a cross-section view of a variable femoral head in a first orientation.
Figure 16B:
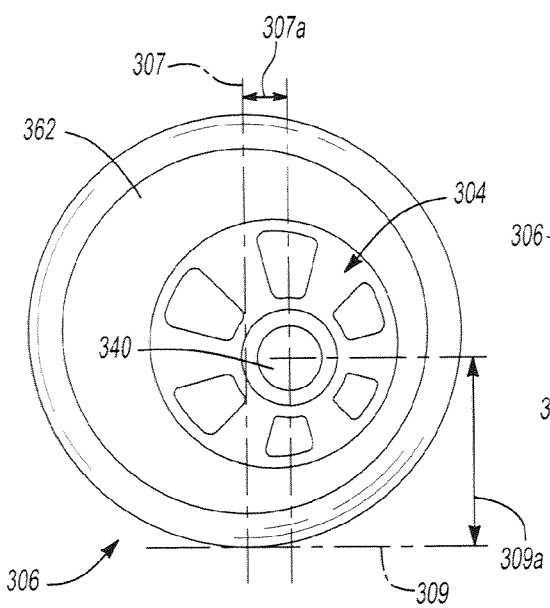
FIG. 16B is a plan view of a variable femoral head in a second orientation.
Figure 16C:
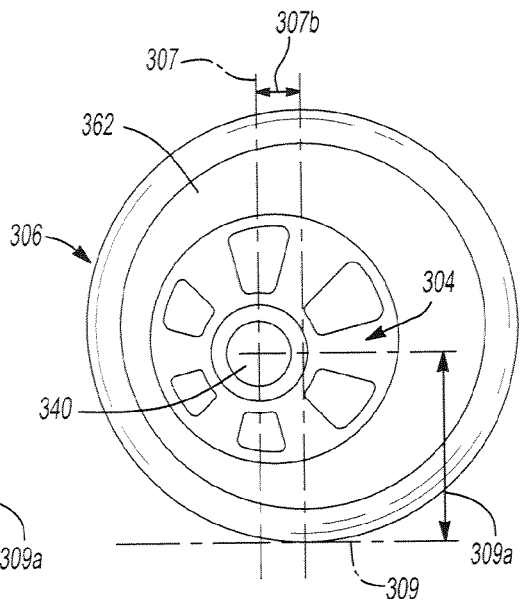

As illustrated in FIGS. 16B and 16C the adapter 304 can also be rotated to move the taper 340 in a direction transverse to a line or axis 307 defined by the back face 362 of the femoral head 304. The line 307 can be a center line of the head, or any other line that is generally in the same plane or parallel to a plane of the back surface 362. Generally, the line 307 is provided to illustrate a "right" or "left" movement of the taper 340 relative to the head 306. "Right" and "left", here, are understood to be relative terms, used to identify relative movement of the taper 340 and not necessarily an actual direction of the taper 340.

Regardless, as illustrated in FIG. 16B the taper 340 can be positioned a distance 307a to the "right" of the line 307. The taper 340, however, is a distance 309a from a line 309 defined relative to the head 306. The adapter 304 can also be rotated relative to the head 306 to place the taper 340 a distance 307b to the "left" of the line 307, as illustrated in FIG. 16C. When the taper 340 is to the "left," however, the taper 340 can maintain the distance 309a from the line 309. Thus, the taper 340 can be rotated "left" or "right" relative to the head 306 (e.g. to create selected anteversion or retroversion offset, as illustrated in FIG. 21). In rotating the adapter 304, however, the taper 340 can also be moved "up" and "down" (again it is understood that "up" and "down" are merely for descriptive differences in position and not necessarily absolute positions of the taper 340) as illustrated in FIG. 16A (e.g. to create selected varus and valgus offset as illustrated in FIG. 20).

Figure 17:
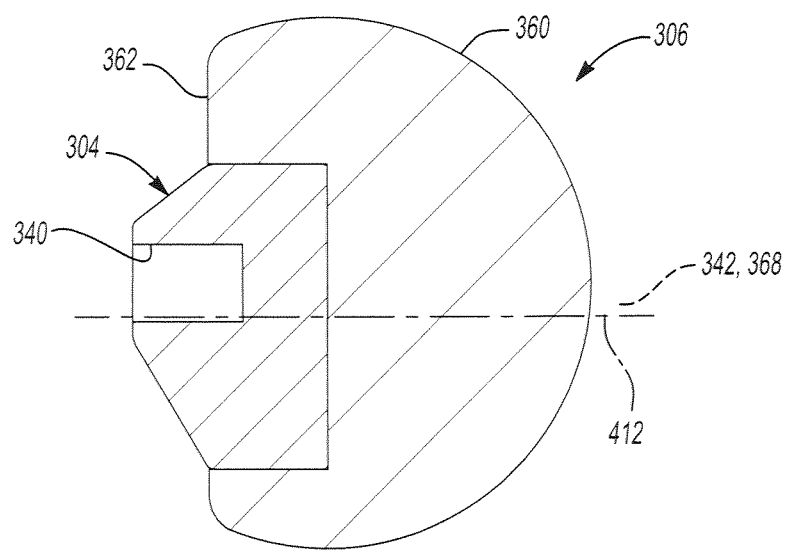
FIG. 17 is a cross-section view of a variable femoral head in a fourth orientation.

By rotating the adapter 304, relative to the femoral head 306, an offset of about, nearly, or exactly zero can also be achieved when the center of the femoral head 368 and the center of the female taper 342 are substantially aligned, as illustrated in FIG. 17. It will be understood that having substantially zero offset can be understood to include a small amount of error offset that is due to manufacturing tolerances, thus, a zero offset may actually be a non-zero amount. However, substantially no offset can be about 0.0 mm to about 0.3 mm, including amount 0.0 mm to about 0.02 mm and further including about 0.01 to about 0.015 mm.

As discussed above, by rotating the adapter 304 relative to the femoral head 306, the selected offset can be achieved between the maximum "UP" offset 410, as illustrated in FIG. 16A and substantially zero offset 412, illustrated in FIG. 17. Additionally, "left" and "right" offset can be achieved by rotating the adapter 304. Accordingly, the single combination of the adapter 304 and the femoral head 306 can allow for a femoral prosthesis to be positioned within the patient at any of the plurality of offsets achievable by rotating the adapter 304 relative to the femoral head 306. Additionally, in various embodiments, the interconnection of the adapter 304 with the femoral head 306 can be achieved with substantially no further adhesives or connection mechanism between the various components, including the adapter 304, the femoral head 306, and the femoral stem 302. It will be understood, however, that in selected embodiments additional connection mechanisms can be provided between the various components. For example, adhesives or other materials can be positioned to interconnect the various components. For example, a mechanical interconnection, such as a screw or the like, can be provided through various tapped or untapped holes formed within the femoral head 306 or the adapter 304. Additionally, as discussed further herein, various portions of the prosthesis, according to various embodiments, can be interconnected with fixation or locking portions to allow for achieving a selected orientation of the femoral head relative to a femoral stem.

Figure 18:
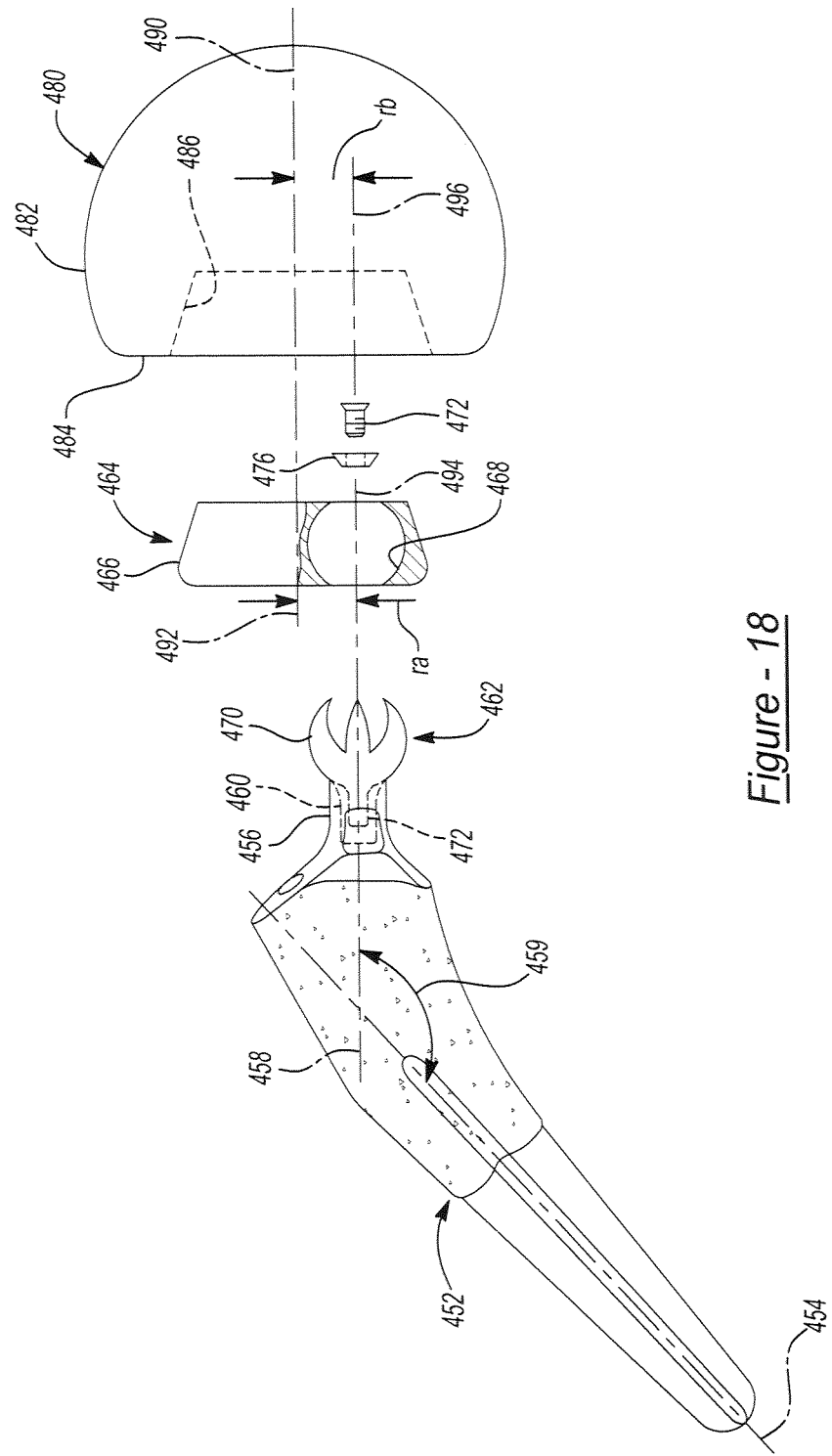
FIG. 18 is an exploded plan view of a variable femoral prosthesis, according to various embodiments.

With reference to FIG. 18, a variable femoral prosthesis 450 is illustrated. The variable femoral prosthesis 450 can be similar to the prosthesis 410 illustrated above in FIG. 11. However, the femoral prosthesis can include a femoral stem 452 that extends along a first axis 454 and a neck portion 456 that extends along a second axis 458. Generally, an angle 459 can be defined between the stem axis 454 and the neck axis 458. The angle 459 can be an appropriate angle, such as an obtuse angle. The neck 456 can further define a bore 460 for receiving a ball stud 462.

The femoral prosthesis 450 further includes an adapter 464. The adapter 464 can define an exterior surface or male taper 466. Additionally, the adapter 464 defines an attachment aperture 468 for rotatable engagement with the ball stud 462. The ball stud 462 includes a divided ball segment 470 through which a fastener 472 can engage an internal bore 474. The fastener 472 first passes through a wedge 476 and fixes the wedge 476 within the divided ball portion 470 once the divided ball portion 470 is in the attachment aperture 468. Accordingly, the wedge 476 can wedge the divided ball portion 470 to engage the attachment aperture 468 and the fastener 472 can hold the wedge relative to the divided ball portion 470 within the adapter 464. Accordingly, the adapter 464 can be fixed relative to the neck 456. The divided ball portion 470 can also be made as one piece with the neck 456.

A femoral head 480 can include an articulation surface 482 similar to the articulation surface of the femoral head 306 discussed above. Additionally, the femoral head 480 can include a stem facing surface 484 into which a female taper 486 is defined. Thus, the articulation surface 482 of the head 480 can define more than a hemisphere or selected portion of a sphere, as discussed above. For example, the articulation surface 482 can be about 55% to about 95% of a sphere, including about 60% to about 80%, inclusive.

The femoral head 480 can define a central axis 490. Additionally, the adapter 464 defines an adapter central axis 492 and an aperture central axis 494 is defined through the adapter and the attachment aperture 468. The central axis 494 through the attachment aperture 468 is eccentric or readily offset by a distance $r_a$ from the central axis 492 of the adapter 464. Additionally, a center axis 496 through the taper 486 in the femoral head 480 can be defined. Accordingly, a radial offset of $r_b$ between the center axes of the head 490 in the center axis of the taper 486 can be formed. In this manner, the center axis 492 of the adapter 464 can be positioned substantially in the center or aligned with the center axis 496 of the taper 486, but is offset by the radial distance $r_b$ from the center of the head axis 490. As discussed above, in relation to FIGS. 11-13, the adapter 464 can be rotated relative to the ball stud 462 and the femoral head 480 can be rotated relative to the adapter 464 to achieve selected radial offsets of the femoral head 480 relative to the femoral neck 456. As discussed above, the adapter 464 can be rotated relative to the ball stud 232 that is fixed and within the neck 456 to achieve selected offsets due to the radial offset $r$, of the center of the ball stud 462 relative to the center axis 492 of the adapter 464. Similarly, rotating the femoral head 480 relative to the adapter 464 achieves a selected offset due to the radial offset $r_b$ of the center axis 490 of the femoral head and center axis 496 of the taper 486. Again, appropriate offsets can be achieved within the range as discussed above for achieving a selected implantation offset within a patient.

With reference to FIG. 19, a femoral prosthesis according to various embodiments can be positioned relative to a pelvis 520 of a patient. The femoral prosthesis can be a part of a system that can include an acetabular prosthesis or a prepared acetabulum. An acetabulum can be prepared to receive a femoral head, such as the femoral head 306 or an acetabular prosthesis 522 can be positioned within the prepared acetabulum 520. It will be understood, however, that the femoral head 306, according to various embodiments, can articulate with the prosthetic acetabulum or with a natural acetabulum. Additionally, the femoral stem can be positioned in a femur 524 such as the femoral stem 302. The adapter 304 can be positioned within the femoral head 306 in an appropriate manner to achieve an alignment along a selected axis, such as an articulation axis 526 to achieve a selected position, such as an anteversion or other offset position, as discussed herein, of the femur 524 relative to the pelvis 520 after implantation. As discussed above, the adapter 304 can be rotated relative to the femoral head 306 to achieve the selected offset.

In implanting and preparing to implant the variable prosthesis, such as the variable femoral prosthesis 300, a surgeon can determine a desired offset, including at least one of an anteversion angle, a retroversion angle, a varus angle, or a valgus angle. In one example, the surgeon can review image data or visually inspect and manually measure the patient to determine a selected or optimal offset. The head, adapter, and stem can then be properly rotated to achieve the selected offset and the variable prosthesis can be implanted. In various embodiments, the surgeon may also re-measure, initially measure, or visually inspect the patient after preparing or implanting at least one of the stem 302 or the acetabular prosthesis 522 to determine an optimal angle or offset. Again, the head, adapter, and stem can then be properly rotated to achieve the selected offset and the variable prosthesis can be implanted based on the measurement and/or determination after preparing or implanting at least one of the stem 302 or the acetabular prosthesis 522. Thus, the determination of the appropriate offset can be made and the appropriate position of the head and adapter can be made at a selected appropriate time.

As an example, an illustrated in FIGS. 20 and 21 the variable femoral prosthesis can be positioned within a patient in the selected offset, which can include a selected anteversion angle, retroversion angle, varus angle, or valgus angle. The offset of the variable prosthesis, however, can be positioned within the patient based upon an orientation of an adapter 304 relative to the femoral head 306 and the femoral stem 302. As discussed above and illustrated in FIGS. 16A and 17, the adapter 304 can be rotated relative to the femoral head 306 to position the taper 340 generally along an axis, but closer to or further away from a central axis that is defined through an apex of the head 306. It will also be understood, however, as illustrated in FIGS. 16B and 16C, that the taper 340 can be rotated relative to a central axis defined generally on a plane defined by the backside of the head 306 to move the taper 340 between two sides of the femoral head 306.

As illustrated, therefore, positions of the taper 304 and the femoral head 306 relative to the femoral stem 302 allows for movement of the femoral head 306 relative to the femoral stem 302. The adapter 304 can be rotated around within the femoral head 306 in substantially 360 degrees. Accordingly, movement of the femoral adapter 304 relative to the femoral head 306 and the stem 302 can form or move the head 306 in a varus direction 550 or a valgus direction 552, as illustrated in FIG. 20. The direction can be based on the patient's anatomy and relative to the femoral stem 302 that defines an axis 302a generally through the stem 302.

In a selected orientation, the femoral head can be aligned with an axis through a trunion 554 or neck of the femoral stem 302, such that the femoral head 306 can include the central axis that is substantially aligned with the axis of the trunion 554. In a selected orientation, however, the rotation of the adapter 304 and/or the femoral head 306 can move the femoral head 306 to a varus direction 550, as illustrated by phantom head position 550a. Alternatively, the adapter 304 and/or the femoral head 306 can be rotated to move the femoral head 306 in a valgus direction 552, as illustrated in phantom head position 552a. The varus and valgus directions, 550, 552, respectively, can be achieved within the anatomy of the patient.

In addition, due to rotation of the femoral head 306 and/or the femoral adapter 304, the femoral head 306 can also be moved in an anteversion direction 560 or in a retroversion direction 562, as illustrated in FIG. 21. Again, the femoral stem 302 can define the central axis 302a and the trunion or neck axis 554 that can be aligned with a central axis of the femoral head 306 in a selected position. The femoral adapter 304 and/or the femoral head 306, however, can be rotated to move the femoral head 306 in an anteversion direction 560 as shown in phantom head position 560a. Alternately, the adapter 304 and/or the femoral head 306 can be rotated to move the femoral head 306 in a retroversion direction 562 as shown by phantom head position 562a. Again, the anteversion and retroversion directions, 560, 562, respectively, can be anatomical positions relative to the femur 524 and the pelvis 520.

Accordingly, movement of the femoral head 306 in any one of the varus directions, valgus direction, anteversion direction, or retroversion direction can be substantially relative to the patient. The rotation of the femoral head 306 and/or the adapter 304 relative to the stem 302 positioned in the femur 524, however, can achieve the various directions relative to the pelvis 520 to achieve a selected position of the femur 524 relative to the pelvis 520. Thus, the combination of the head 306 and the adapter 304 can achieve various and selection offsets of the head 306 relative to the stem 302.

It is understood that the implantation of the femoral prosthesis, according to various embodiments, can be achieved with generally known surgical techniques. Generally, access can be achieved to the femoral joint and either or both of the femur 524 and the pelvis 520 can be prepared for implantation for selected prostheses. The variable prosthesis as discussed herein, however, can allow for a physician or surgeon to implant a prosthesis with an appropriate offset, as discussed above, even after preparing the acetabulum and the femur to maintain a selected amount of bone after implantation or based upon an anatomy or bone structure of a patient. For example, achieving a position of a fixed or non-variable prosthesis relative to a patient may be difficult if a bone structure or anatomy does not allow for extensive reaming or preparation for various prostheses. Nevertheless, the prosthetic devices can be specifically designed for selected patients, but a variable prosthesis can minimize selection and minimize inventory at a selected implantation facility therefore allowing greater variability with a single prosthetic device for multiple patients.

In reference to all of the above-described embodiments, various tapered surfaces have been referenced at interfaces between the stem, adapter and head. In one example, these tapered surfaces are configured as self locking tapers, such as morse-type tapers which provide a self locking interface. Locking tapers can include complementary angles of about 3 degrees to about 5 degrees, inclusive. While morse-type tapers are described herein, one skilled in the art will readily recognize that other means may be incorporated for providing a locking interface between the various components of the prosthesis system. In this regard, one or more interfaces may be interlocked with the use of an additional fastener to insure locking engagement therebetween.

Moreover, the various components can be formed with generally known techniques. For example, the heads, adapters and stems can be formed with various forging or casting techniques and selected finishing procedures can be applied to their respective surfaces. The tapers can also be formed in the various components with selected milling techniques or can be formed with casting and forging techniques.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. A method of implanting a femoral prosthesis system in a patient, comprising:
    determining an anteversion angle of a natural femur relative to a pelvis of the patient;
    selecting an adapter having an adapter center axis and an adapter offset connection, wherein the adapter offset connection has an adapter connection center axis;
    selecting a femoral head having a head center axis and an offset head connection, wherein the offset head connection has a head connection center axis; and
    rotating the selected adapter relative to the selected femoral head to achieve a selected offset of the adapter connection center axis relative to the head connection center axis;
    wherein the selected offset of the adapter connection center axis relative to the head connection center axis is based on the determined anteversion angle;
    wherein the adapter has a first side, an opposing second side, an outer surface defining a male taper, and a stem facing taper surface that defines at least one straight line extending from the first side to the outer surface and configured to provide clearance between the adapter and a femoral stem.

2. The method of claim 1, wherein the adapter offset connection includes a female locking taper.

3. The method of claim 2, wherein the adapter connection center axis is defined substantially through a center of the adapter offset connection.

4. The method of claim 1, wherein rotating the selected adapter relative to the selected femoral head to achieve the selected offset of the adapter connection center axis relative to the head connection center axis includes achieving the selected offset at or between a maximum offset and substantially zero offset.

5. The method of claim 4, wherein selecting the femoral head includes selecting a femoral head member having a curved articulating surface configured to articulate relative to the pelvis when replacing the natural femur.

6. The method of claim 5, wherein selecting the femoral head further includes selecting the femoral head member to include a substantially planar surface opposed to the curved articulating surface and configured to interconnect with a femoral stem configured to be implanted into the femur.

7. The method of claim 4, wherein the maximum offset is defined as positioning the adapter connection center axis away from the head center axis a maximum distance.

8. The method of claim 4, wherein substantially zero offset is defined as substantially aligning the adapter connection center axis and the head center axis.

9. A method of implanting a femoral prosthesis system in a patient, comprising:
forming a femoral head having:
an articulating surface that defines a curve and an opposed surface to the articulating surface, and
a head female taper formed into the femoral head through the opposed surface, wherein a head center axis of the femoral head is offset a first radial distance from a head taper center axis of the head female taper;
forming an adapter having:
a first side and an opposed second side,
an outer surface defining an adapter male taper and an adapter female taper formed into the adapter from the first side, wherein the adapter has an adapter center axis offset a radial distance from an adapter female taper axis; and
forming a femoral stem having a body and a neck, wherein the neck extends at an angle relative to the body and the neck has an outer surface that defines a neck male taper, the adapter including a stem facing taper surface defining at least one line with a constant slope extending from the first side to the outer surface and configured to provide clearance between the adapter and the femoral stem.

10. The method of claim 9, further comprising:
determining an anteversion angle of a femur relative to a pelvis of the patient.

11. The method of claim 10, further comprising:
connecting the femoral head, the adapter, and the neck to achieve a selected femoral head offset relative to the femoral stem based on the determined anteversion angle.

12. The method of claim 11, further comprising:
rotating the adapter relative to the femoral head to achieve the selected femoral head offset.

13. The method of claim 9, wherein forming the femoral head includes forming the head center axis of the femoral head through a center of the articulating surface and forming the head taper center axis of the head female taper through a center of the head female taper.

14. The method of claim 9, wherein forming the adapter includes forming the adapter center axis of the adapter through a center of the adapter, and forming the adapter female taper axis of the adapter female taper through a center of the adapter female taper.

15. A method of implanting a femoral prosthesis system in a patient, comprising:
selecting a femoral head having a head center axis and an offset head connection, wherein the offset head connection has a head connection center axis that is displaced a distance from the head center axis; wherein the selected femoral head further has a first curved articulating surface configured to articulate near a pelvis when implanted into a femur;
selecting an adapter having an adapter center axis and an adapter offset connection, wherein the adapter offset connection has an adapter connection center axis that is displaced a distance from the adapter center axis; and
rotating the selected adapter relative to the selected femoral head to achieve a selected offset that is an offset distance of the adapter connection center axis and to the head connection center axis;
wherein the selected offset of the adapter connection center axis relative to the head connection center axis is based on a determined anteversion angle of a femur relative to a pelvis of the patient;
wherein the adapter has a first side, an opposing second side, an outer surface defining a male taper, and a stem facing taper surface extending from the first side to the outer surface and configured to provide clearance between the adapter and a femoral stem, wherein the adapter in cross-section defines at least one straight line on the stem facing taper surface.

16. The method of claim 15, further comprising:
measuring a position of the femur relative to an acetabulum in the pelvis to determine the anteversion angle.

17. The method of claim 16, further comprising:
obtaining access to a hip joint between the femur and the pelvis;
resecting a natural femoral head of the femur; and
implanting the selected femoral head to replace the resected femoral head.

18. The method of claim 17, further comprising:
selecting the offset distance to be the selected offset, wherein the selected offset is at or between a maximum offset and a minimum offset;
wherein the maximum offset is a maximum displacement of the adapter connection center axis and the head center axis;
wherein the minimum offset is a substantial alignment of the adapter connection center axis and the head center axis.

19. The method of claim 18, further comprising:
implanting a femoral stem into the femur;
connecting the selected adapter to the femoral stem; and
connecting the selected femoral head to the selected adapter.

20. The method of claim 19, wherein connecting the selected femoral head to the selected adapter includes fixing the selected femoral head to the selected adapter;
wherein fixing the selected femoral head to the selected adapter occurs after rotating the selected adapter relative to the selected femoral head to achieve the selected offset.

* * * * *